United States Patent [19]
Baxter et al.

[11] Patent Number: 5,258,287
[45] Date of Patent: Nov. 2, 1993

[54] DNA ENCODING AND METHODS OF PRODUCTION OF INSULIN-LIKE GROWTH FACTOR BINDING PROTEIN BP53

[75] Inventors: Robert C. Baxter, Plebe, Australia; William I. Wood, San Mateo, Calif.

[73] Assignees: Genentech, Inc., South San Francisco, Calif.; Central Sydney Area Health Service, Camperdown, Australia

[21] Appl. No.: 171,623

[22] Filed: Mar. 22, 1988

[51] Int. Cl.⁵ .............. C12N 5/10; C12N 1/15; C12N 1/21; C12N 15/12
[52] U.S. Cl. .............. 435/69.1; 536/23.5; 435/6; 435/69.8; 435/240.1; 435/240.2; 435/252.3; 435/254.11; 435/254.2; 435/320.1
[58] Field of Search .............. 435/69.1, 6, 172.3, 435/69.8, 320.1, 254, 255, 256, 240.2, 240.1; 536/27

[56] References Cited

U.S. PATENT DOCUMENTS

| | | | |
|---|---|---|---|
| 4,853,330 | 8/1989 | Goeddel et al. | 435/226 |
| 4,868,113 | 9/1989 | Jaye et al. | 435/70 |
| 4,886,747 | 12/1989 | Derynck et al. | 435/69.4 |
| 4,925,793 | 5/1990 | Goeddel et al. | 435/69.51 |
| 4,963,665 | 10/1990 | Rotwein | 435/69.1 |
| 5,010,002 | 4/1991 | Levinson et al. | 435/69.2 |
| 5,028,531 | 7/1991 | Ueda et al. | 435/69.4 |
| 5,089,396 | 2/1992 | Mason et al. | 435/69.1 |
| 5,098,833 | 3/1992 | Lasky et al. | 435/69.1 |

FOREIGN PATENT DOCUMENTS

| | | |
|---|---|---|
| 183070 | 6/1986 | European Pat. Off. |
| 244234 | 11/1987 | European Pat. Off. |
| 0294021 | 12/1988 | European Pat. Off. |
| 321196 | 6/1989 | European Pat. Off. |
| 0369943 | 5/1990 | European Pat. Off. |
| 0375438 | 6/1990 | European Pat. Off. |
| WO8908667 | 9/1989 | PCT Int'l Appl. |
| WO8909792 | 10/1989 | PCT Int'l Appl. |

OTHER PUBLICATIONS

Suggs et al *Proc Natl Acad Sci*, vol. 78(11) pp. 6613-6617 Nov. 1981 "Use of Synthetic . . .".
Palva, I. et al., *Gene*, 22: 229-235, 1983.
Brewer, M. T. et al., *Biochem. Biophys. Res. Comm.*, 152(3): 128-97, 1988.
Stinchcomb, D. T. et al., *Nature*, 282: 39-43, 1979.
Beach, D. et al., *Nature*, 290: 140-42, 1981.
de Louvencourt, L., *J. of Bacteriology*, pp. 737-742, 1983.
Case, M. E. et al., *PNAS*, 76 (10): 5259-5263, 1979.
Ballance, D. J. et al., *Biochem. Biophys. Res. Comm.*, 112(1): 284-9, 1983.
Tilburn, J. et al., *Gene*, 26: 205-21, 1983.
Yelton, M. M. et al., *PNAS*, 81: 1470-74, 1984.
Kelly, J. M. et al., *EMBO J.*, 4(2): 475-79, 1985.
Stepien, P. P. et al., *Gene*, 24: 289-97, 1983.
Hitzeman, R. A. et al., *Science*, 219: 620-25.
Tuite, M. F., *EMBO J.*, 1(5): 603-608, 1982.
Miyohara, A., *PNAS*, 80: 1-5, 1983.
Hitzeman, R. A., *NAR*, 11(9): 2745-2763, 1983.
Luckow, V. A. et al., *Bio/Technology*, 6: 47-55, 1988.
Setlow, J. K. et al., editor, *Genetic Engineering*, pp. 277-297.
Maeda, S. et al., *Nature*, 315: 592-594, 1985.
Depicker, A. et al., *J. of Mol. Appl. Genetics*, 561-73, 1982.

(List continued on next page.)

Primary Examiner—Robert J. Hill, Jr.
Assistant Examiner—Marianne Porta Allen
Attorney, Agent, or Firm—Janet E. Hasak

[57] ABSTRACT

DNA isolates coding for insulin-like growth factor binding protein may be used to produce the protein via recombinant expression systems. Insulin-like growth factor binding protein, which generally has a molecular weight of about 53 kD on non-reducing SDS-PAGE, is useful as a binder to insulin-like growth factor and as a metabolic regulator.

20 Claims, 15 Drawing Sheets

OTHER PUBLICATIONS

Derynck, R. et al., *Nature* 316, 701–705 (1985).
Sharples, K., et al., *DNA*, 6(3): 239–244 (1987).
*BNA's Patent, Trademark & Copyright Journal* 43, 116–118 (1991).
Spratt, S. K., et al., *Growth Factors* 3, 63–72 (1990).
Sommer et al., *Modern Concepts of Insulin-Like Growth Factors*, E. M. Spencer ed., (Elsevier Science Publishing Co., Inc.) pp. 715–728 (1991).
Baxter, R. C. and Cowell, C. T., J. Clin. Endo. and Metab. 65: 432–440 (1987).
Baxter, R. C. and Martin, J. L., Biochem. Biophys. Res. Commun. 147: 408–415 (1987).
Baxter, R. C., and Martin, J. L., J. Clin. Invest. 78: 1504–1512 (1986).
White, R. M. et al., J. Clin. Endo. and Metab. 53: 49–57 (1981).
Martin, J. L. et al., J. Clin. Endo. and Metab. 61: 799–801 (1985).
Daughaday et al., J. Clin. Endo. and Metab. 55: 916–921 (1982).
Martin, J. L. and Baxter, R. C., J. Biol. Chem. 261: 8754–8760 (1986).
Baxter, R. C. et al., Biochem. Biophys. Res. Commun. 139: 1256–1261 (1986).
Hintz, R. L., Clinics in Endo. and Metabol. 13: 31–42 (1984).
Wood et al., Molecular Endocrinology, 2: 1176–1185 (1988).
Leung et al., Nature, 330: 537–543 (1987).
Oshima et al., *J. Biol. Chem.*, 263: 2553–2562 (1988).
Brinkman et al. The EMBO Journal, 7: 2417–2423 (1988).
Lee et al., *Molecular Endocrinology*, 2: 404–411 (1988).
Grundmann et al., *Nucl. Acids Res.*, 16:8711 (1988).
Martin, et al., *J. Biol. Chem.* 261: 8754–8760 (1986).
Baxter et al., *Comp. Biochem. Physiol.*, 91B: 229–235 (1988).

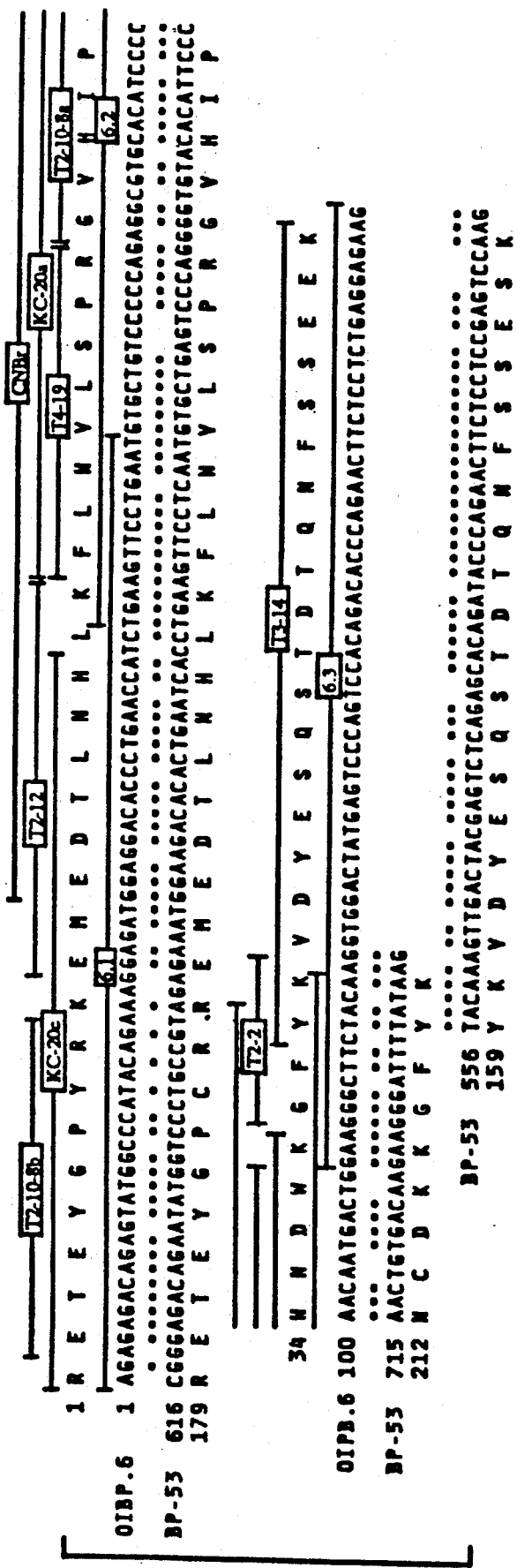

```
             1  G A S S A G L G P Y V R C E P C D A R A L A Q C A P P A V C A E
OIBP.9       1  GGCGCCTCTGCTGGCCTGGGCCCTTATGTGAGATGTGAGCCATGTGATGCCAGAGCCCTGGCCCAGTGTGCCCCCCCAGCTGTCTGCTGAG
                ····· ··· ···· ·· ····· ····· ·· ·· ····· ·· ········· ·· ····· ····· ····· ·· ·· ·····
BP-53       82  GGCCGAGCTCGGGCTTGGGCCCCGGGGTCCGCTGCGAGCCCTGCGACGCCCGCGCCCTGGCCCAGTGCGCCCCCCCTGCTGTGTGCGAG
             1  G A S S G G L G P V V R C E P C D A R A L A Q C A P P A V C A E

34  L V R E P G C G C L L C A L C E G Q P P
OIBP.9     100  CTGGTGAGAGAGCCTGGCTGTGGCTGTCTGCTCTGTGCCCTGTGTGAGGGCCAGCCCCCC
                ····· ····· ··· ····· ·· ·· ····· ··· ····· ·· ········· ··
BP-53      181  CTGGTGCGCGAGCCGGGCTGCGGCTGCCTGCTCACTTGCGCACTGAGCGAGGGCCAGCCGTGC
            34  L V R E P G C G C L L T C A L S E G Q P C
```

FIG.IC

```
            1  A Y L L P A P P A P G N A S E S E E D D
T2-15
OIBP.2      1  GCCTACCTGCTGCCCGCCCCCGCCCCTGGCAATGCCTCTGAGTCTGAGGAGGATGAC
               ········· ·· ····· ·· ·· ····· ·· ·····     ····· ·· ·····
BP-53     373  GCCTACCTGCTGCCAGCCCCAGCTCCAGGAAATGCTAGTGAGTCGGAGGAAGACCGC
           98  A Y L L P A P P A P G N A S E S E E D R
```

```
                        SACI
                                                                PVUII
                                                             PFUMI                                                                                       PFLMI
 892 TTAATGTGGA GCTCAAATAT GCCTTATTTT GCACAAAGA CTGCCAAGGA CATGACCAGC AGCCTGGCTAC AGCCTCGATT TATATTTCTG TTTGTGGTGA
 992 ACTGATTTTT TTAAACCAA AGTTAGAAA GAGGTTTTG AAATGCCTAT GCTTCCTTTG AATGGTAAAC TTGAGCATCT TTTCACTTTC CAGTAGTCAG
                                XHOI
1092 CAAAGAGCAG TTTGAATTTT CCTATCAAA TATTCAGAGA CTCGAGCACA GCACCCAGAC TTCATGCGCC CGTGGAATGC TCAACCACATG
1192 TTGGTCGAAG CGGCCGACCA CTGACTTGT GACTTAGGCG CTGTGTTGC CTATGTAGAG AACACGCTTC ACCCCACTC CCCGTACAGT GCGCACAGGC
                                                 SACI
1292 TTTATCGAGA ATAGGAAAAC CTTTAAACCC CGGTCATCCG GACATCCCAA CCCATGCTCC TGGAGCTCAC AGCCTCTGT GGTGTCATTT CTGAAACAAG
1392 GCGTGGATC CCTCAACCAA GAAGAATGTT TATGTCTTCA AGTGACCTGT ACTGCTTGG GACTATTGGA GAAATAAGG TGGAGTCCTA CTTGTTTAAA
1492 AAATATGTAT CTAAGAATGT TCTGGGAACC TATAAAGGCA GGTATTTCGG CCCTCCTCT TCAGGAATCT TCCTGAAGAC ATGGCCCAGT
1592 CGAAGCCCA GGATGCCTT TGCTGCGCC CCGTGGGTA GGAGGACAG AGAGACGGGA GAGTCAGCCT CCACATTCAG AGGCATCACA AGTAATGCCA
                                                          HINDIII                                                HINDIII
1692 CAATTCTTCG GATGACTGCA GAAATAGTG TTTTGTAGTT CAACAACTCA AGACGAAGCT TATTCTGAG GATAAGCTCT TTAAAGGCAA AGCTTTATTT
       PSTI                                                                                                              PSTI
1792 TCATCCTCA TCTTTGTCC CCTTAGCAC AATGTAAAA AGAATAGTAA TATCAGAACA GGAGGAGGA ATGGCTTGCT GGGCAGCCCA TCCAGGACAC
1892 TGGAGCACA TAGAGATTCA CCCATGTTG TTGAACTTAG AGTCATTCTC ATGCTTTTCT TTATAATTCA CACATATATG CAGAGAAGAT ATGTTCTTGT
1992 TAACATTGTA TACAACATAG CCCAAATAT ATCCTAGATC ATCCTAGATCT GCTGCTCTCC CGGAGGCCAA ACCCAAGAAG GTCTCAAGA CATTCTGCCT ACCTATTAGC TTTTCTTTAT TTTTTAACT
       SACI        PFLMI                                                                                                         PSTI
2092 TGAGGAAAGG AGCTCACGCC CAGAGACTGG GCTGCTCTCC GTCTCCCTTG AAAACAGAGG GTCAGGCTCA GGAGACTCT GCCCTGCTGC
       SACI
2192 AGACCTCGGT GTGGACACAC GCTGCATAGA GCTCTCCTTG TCTCCCTTG AAAACAGAGG CATTCTGCCT ACCTATTAGC TTTTCTTTAT TTTTTAACT
2292 TTTTGGGGG AAAGTATTT TTGAGAAGTT TGTCTTGCAA TGTATTTATA AAGTTTTA CCATTAAAA AAAAAAAA AAAAAAAA
2392 AAAAAAAAA AAAAAAAA AAAAAAAA
```

FIG. 3-2

DNA ENCODING AND METHODS OF PRODUCTION OF INSULIN-LIKE GROWTH FACTOR BINDING PROTEIN BP53

BACKGROUND OF THE INVENTION

1. Field of Invention

This invention relates to an insulin-like growth factor binding protein acid to the means and methods for its production in therapeutically significant quantities.

2. Description of the Background Art

Peptides of the insulin-like growth factor (IGF) family, the recombinant production of which is described, e.g., in EP 128,733 published Dec. 19, 1984, to Lee et al., are found associated with binding proteins in the circulation, in other body fluids, and in media conditioned by cultured cells. Two IGF binding proteins, found in different fluids, have been identified and characterized. Hintz, R. L. (1984) *Clinics in Endo. and Metabol.*, 13: 31-42; Martin, J. L. and Baxter, R. C. (1986) *J. Biol. Chem.*, 261: 8754-8760; Povoa et al. (1984) *Eur. J. Biochem.*, 144: 199-204. One predominates in adult serum, while the other is found in highest concentrations in amniotic fluid. Baxter et al. (1987) *J. Clin. Endo. and Metabol.*, 65: 423-431.

The levels of the binding protein in adult serum have been found to reflect the growth hormone (GH) status of individuals who are either GH-deficient or acromegalic. Thus, high levels of binding protein correlate with high levels of GH. Martin and Baxter (1985) *J. Clin. Endo. and Metabol.*, 61: 799-801. Thus, this binding protein has been referred to as the GH-dependent IGF binding protein. For convenience, the designations BP53 for the GH-dependent binding protein from human plasma and BP28 for the binding protein first isolated from amniotic fluid are used herein. The designations indicate the size of the purified proteins on non-reducing sodium dodecyl sulfate polyacrylamide gel electrophoresis (SDS-PAGE).

BP53 is found as an acid-stable component of a 125-150 kD glycoprotein complex contained in human plasma that carries most of the endogenous IGFs and is also regulated by GH. White et al. (1981) *J. Clin. Endo. and Metabol.*, 53: 49ff; Hintz et al., *J. Clin. Endo. and Metabol.*, 53: 100ff; and Daughaday et al. (1982) *J. Clin. Endo. and Metabol.*, 55: 916ff. The binding component of this complex, purified after acidification, has a molecular weight on SDS-PAGE of 43 kD (reduced) and 53 kD (non-reduced). The purified protein has a high affinity for IGF-I and IGF-II ($K_a = 20-40$ nM$^{-1}$). Martin and Baxter, *J. Biol. Chem., op cit.* The concentration of BP53 in normal adult plasma is 6.1 mg/l. The levels of BP53 are increased in acromegalic subjects to 13.5 mg/l and decreased in GH-deficient subjects to 2-3 mg/l. Baxter and Martin, *J. Clin. Invest.*, 78: 1504-1542 (1986). While BP28 predominates in amniotic fluid, BP53 is also found in amniotic fluid at about 4.6 mg/l. The rat homolog of BP53 has been purified, and it has considerable N-terminal amino acid sequence homology with the human protein. Baxter and Martin (1987) *Biochem. Biophys. Res. Comm.*, 147: 408-415.

BP28 has a molecular weight of 35-40 kD as determined by gel filtration chromatography (Drop et al. (1984) *J. Clin. Endo. and Metabol.*, 59: 899ff), similar to the 32 kD (reduced) or 28 kD (non-reduced) molecular weight found on SDS-PAGE. The purified protein binds both IGF-I and IGF-II, but with a lower affinity than BP53 ($K_a = 3-7$ nM$^{-1}$). Concentrations from 37 to 148 mg/l have been reported by Baxter et al., supra, for BP28 in amniotic fluid. While BP53 predominates in adult serum, BP28 is present in serum where its concentrations range from 0.02 to 0.35 mg/l with a marked diurnal cycle peaking at 0600 to 0800 hours. Baxter and Cowell (1987) *J. Clin. Endo. and Metabol.*, 65: 432-440. No such diurnal variation has been found for BP53. N-terminal amino acid sequence data show that two other human proteins, PP12 isolated from placenta (Koistinen et al. (1986) *Endocrin.*, 118: 1375ff) and an IGF binding protein isolated from the culture medium of a hepatoma cell line (HEP-G2) (Povoa et al. (1985) *Biochem. Biophys. Res. Comm.*, 128: 1071ff), are the same or closely related to BP28. An IGF binding protein has also been isolated from the culture medium of the rat cell line, BRL-3A. Lyons and Smith (1986) *Mol. Cell. Endo.*, 45: 263-270; Mottola et al. (1986) *J. Biol. Chem.*, 261: 11180-11188. Based on similar size properties, high fetal serum concentration, and some protein sequence similarity, it is likely that this IGF binding protein is the rat homolog of BP28.

Although the isolation and purification of BP53 has been described in the literature as shown above, the relatively low concentration of the protein in human plasma and the high cost, both in terms of effort and expense, of recovering in commercial quantities purified protein from the plasma hinder its broad-scale use, either alone or in combination with IGF.

Accordingly, it is an object of the present invention to isolate DNA encoding BP53 and to produce commercially useful quantities of the protein from a therapeutically acceptable source.

It is a further object to obtain BP53 in a form unaccompanied by the glycosylation associated with the native BP53.

It is an additional object to prepare amino acid sequence and other variants of BP53 that do not substantially adversely affect the biological activity of the protein.

It is yet another object to produce BP53 completely free of other naturally occurring (source) proteins.

These and other objects of the invention will be apparent from the specification as a whole.

SUMMARY OF THE INVENTION

The objects of this invention are accomplished by expression of BP53 in recombinant cell culture, a process that fundamentally comprises providing nucleic acid encoding BP53, transforming host cells with the BP53-encoding nucleic acid, and culturing the cells to express the protein in the host cell culture.

In one specific embodiment, this invention encompasses an isolated DNA sequence comprising a sequence that encodes BP53 wherein said DNA sequence is selected from the group consisting of:

(a) the DNA sequence set forth in FIG. 3; and (b) DNA sequences that hybridize under stringent conditions to the DNA sequence defined in (a) and contain at least about ten nucleotides.

The DNA sequence may also be characterized as comprising a sequence encoding a protein having an amino acid sequence sufficiently duplicative of that of BP53 to allow it to possess the biological property of (1) binding IGF, or (2) cross-reacting immunologically with an antibody raised against at least one epitope of the corresponding native protein.

In other embodiments, the invention relates to (1) labeled DNA sequences for assay purposes, (2) DNA sequences operably linked to a promoter, (3) expression vectors comprising the DNA sequence described above operably linked to control sequences recognized by a host transformed by the vector, and (4) host cells transformed with the expression vector described above. Expression vectors containing both BP53 and IGF are also contemplated herein, so as to enable expression of both proteins together by the host cell.

Further aspects of the invention are directed to novel forms of BP53, including BP53 that is unaccompanied by associated native glycosylation, has at least about 80% homology with the amino acid sequence of the mature protein shown in FIG. 3, and possesses one or both of the biological properties of (a) binding IGF, or (b) cross-reacting immunologically with at least one epitope of the corresponding native binding protein. Such BP53 is generally obtained as a product of expression in heterologous recombinant cell culture. BP53 in any form as a component of a recombinant cell culture is novel.

In a further embodiment, the invention is directed to a pharmaceutical composition useful for binding IGF, comprising a therapeutically effective amount of the BP53 protein of this invention in a pharmaceutically acceptable carrier.

Also contemplated are pharmaceutical compositions useful for metabolic regulation in mammals comprising therapeutically effective amounts of IGF and the BP53 of this invention in a pharmaceutically acceptable carrier.

A diagnostic composition useful for assaying the levels of IGF in circulating human plasma is also encompassed herein, comprising the BP53 of this invention covalently bound to a detectable label moiety.

The present invention makes it possible to produce BP53 and/or derivatives thereof by recombinant techniques, as well as to provide products and methods related to such production. The procedures involved to obtain BP53 recombinantly were not straight-forward, as the N-terminal sequence information for the first 15 amino acids provided by Martin and Baxter, op. cit., was not sufficient to obtain a probe for screening a library for the correct clones. No complete amino acid sequence for BP53 was known heretofore. A longer internal sequence was necessary to obtain the hybridization probes needed to identify clones with sequences encoding BP53. In addition, identification of the correct clones was only obtained upon using three separate pools of four probes simultaneously, and the spots that represented the correct clones were weak.

This invention also enables the production of BP53 in association with a membrane anchor to allow the IGF to be effectively delivered better to a target cell. This may be achieved by introducing at the C terminus of the BP53 protein, by recombinant means or otherwise, an amino acid sequence constituting the transmembrane or membrane-binding domain of the normal receptor for either IGF-I or IGF-II or a phospholipid anchor domain. In this case the BP53 variant is recovered from host cell membrane preparations. Alternatively, the BP53 may be secreted into the extracellular medium of the host cell.

The utility of the BP53 protein and variants thereof resides in binding IGF species present in vitro and in vivo. Thus, it is believed that BP53 can be used to prolong the circulatory half-life of IGF. Without an intent to be held to any one particular theory, it is believed that this increase occurs because of sequestration of the IGF by the BP53, which may serve as a controlled release reservoir for IGF.

Moreover, BP53 may find use as a diagnostic agent for levels of IGF. In addition, the BP53 herein is immunologically cross-reactive with an antibody preparation that has an epitope recognized by the corresponding native BP53, thereby making the BP53 herein useful as a diagnostic reagent for such antibodies.

Other uses for BP53 will be apparent to those skilled in the art.

BRIEF DESCRIPTION OF THE DRAWINGS

FIGS. 1A-D depicts the oligonucleotide probe sequences used to screen human liver libraries for cDNA clones for BP53, as well as the match to the cDNA sequence obtained.

FIG. 10 depicts results of assays of expression of BP53 in mammalian cells.

DESCRIPTION OF THE PREFERRED EMBODIMENTS

Figures 1, 4:
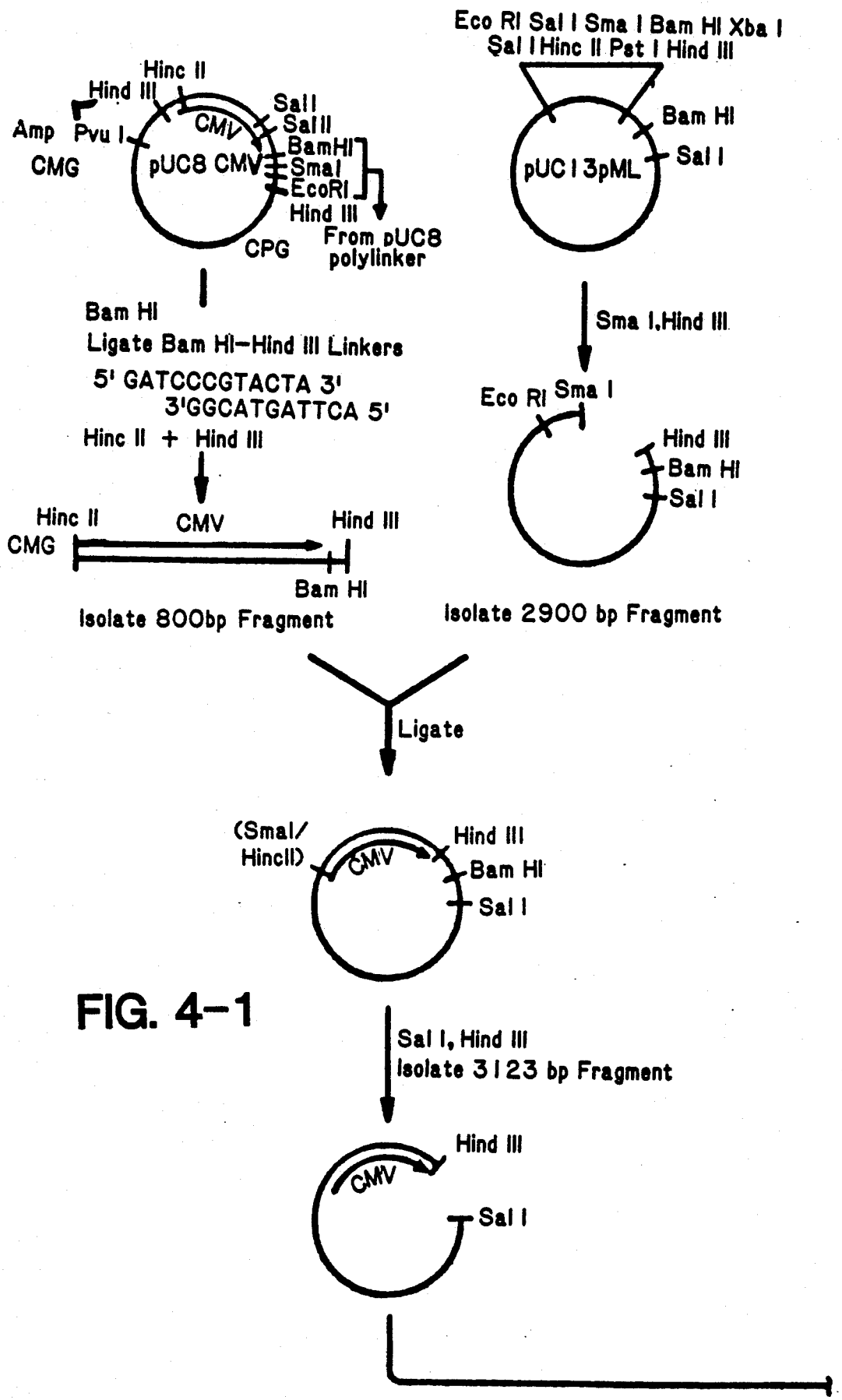
FIG. 4 depicts the construction of the starting expression vector pF8CIS used to construct the ultimate expression vector.
Figures 2, 4:
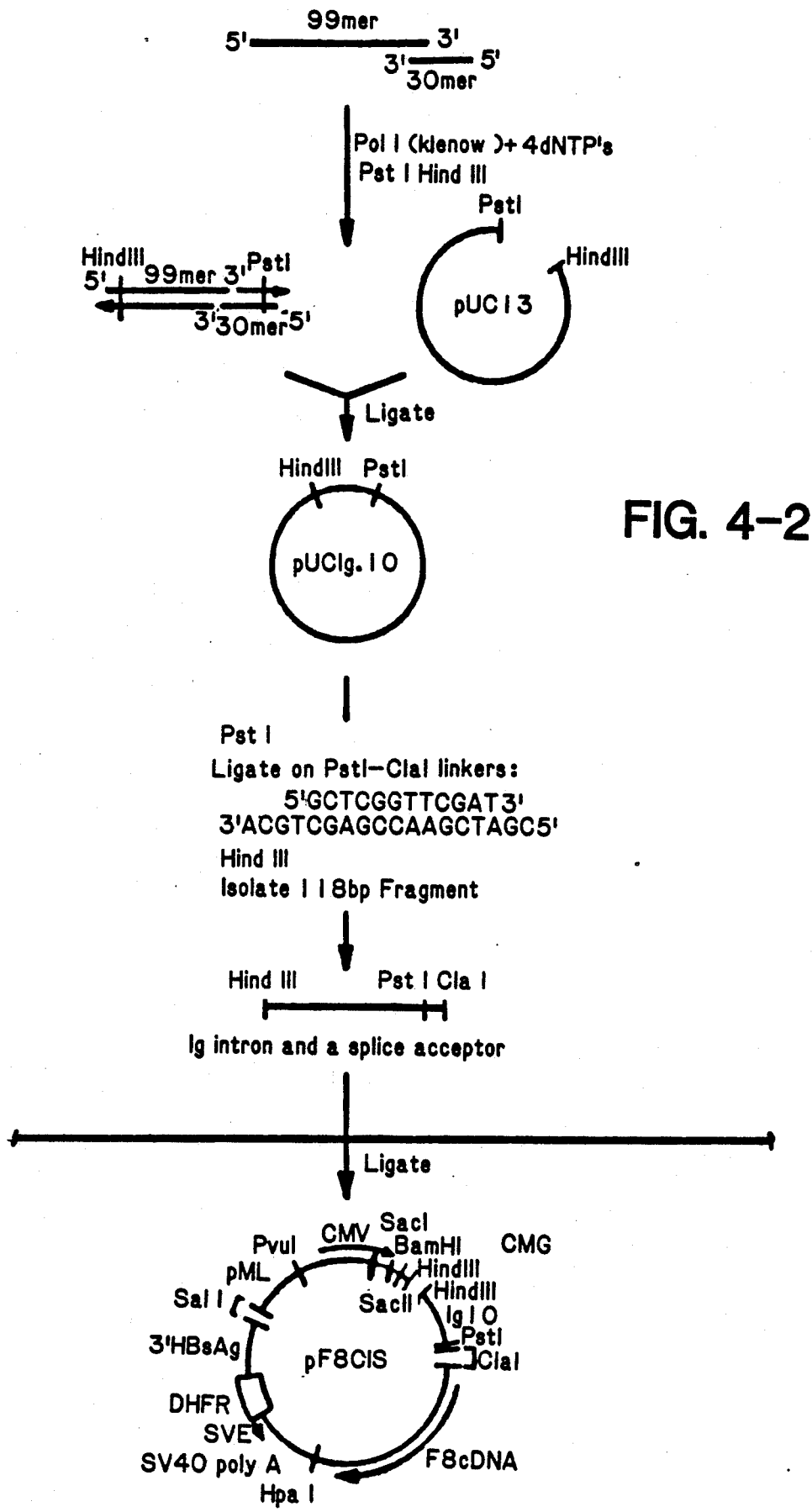
Figures 3, 4:
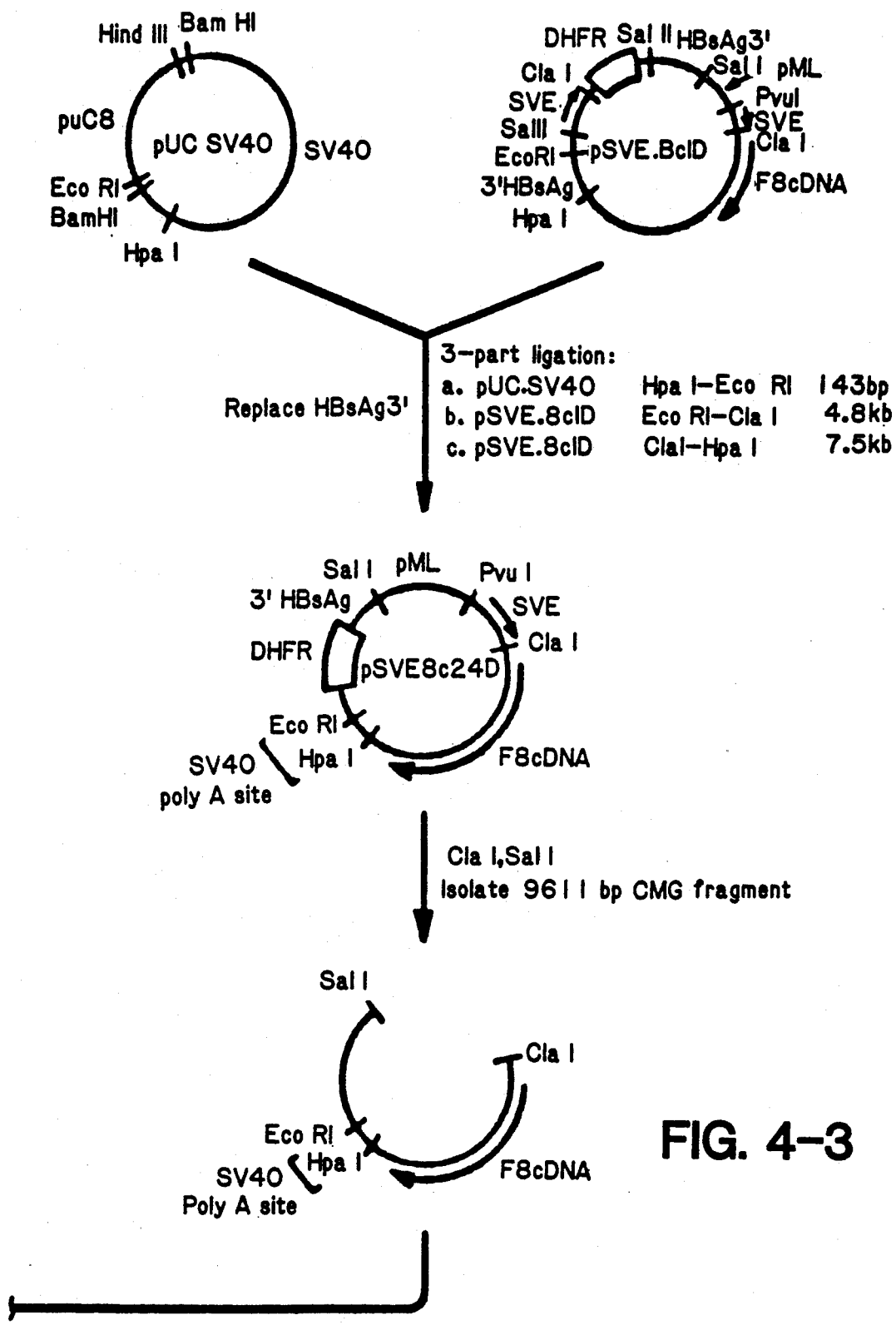
FIG. 3 depicts the nucleotide and predicted amino acid sequence of human BP53 from cDNA clone ibp.118. Predicted amino acids of the protein are shown below the DNA sequence and are numbered from the first residue of the N-terminus of the protein sequence. Negative amino acid numbers refer to the presumed leader signal sequence or preprotein, while positive numbers refer to the mature protein. The location of the sequenced peptides is indicated by underlining. Residues that were uncertain or unidentified upon amino acid sequence determination are indicated by a dot.

As used herein, "insulin-like growth factor binding protein," or "BP53," refers to a mammalian insulin-like growth factor binding protein having the amino acid sequence of FIG. 3, together with analogues and variants thereof having the biological activity of native BP53. The biological activity of native BP53 is shared by any analogue or variant thereof that is capable of specifically binding IGF (normally IGF-I or IGF-II) or that possesses an immune epitope that is immunologically cross-reactive with an antibody raised against at least one epitope of native BP53. Analogues or variants are defined as molecules in which the amino acid sequence, glycosylation, or other feature of native BP53 has been modified covalently or noncovalently. Thus, variants may or may not have a molecular weight of 53 kD (as determined by SDS-PAGE carried out in the absence of a reducing agent such as, e.g., β-mercaptoethanol or dithiothreitol). For example, unglycosylated BP53 having the native mature sequence will have a molecular weight of about 28.7 kD on non-reducing SDS-PAGE. Amino acid sequence variants include not only alleles of the FIG. 3 sequence, but also predetermined mutations thereof. Generally, amino acid sequence variables have an amino acid sequence with at least about 80% homology, and more typically at least about 90% homology, to that of the native BP53 of FIG. 3. Henceforth, the term BP53 shall mean either the native sequence or variant form unless otherwise appropriate.

Included within the scope of the present invention is BP53 having native glycosylation and the amino acid sequence as set forth in FIG. 3, analogous BP53 proteins from other animal species such as bovine, equine, porcine, ovine, canine, murine, feline, and the like, deglycosylated or unglycosylated derivatives of such BP53 proteins, and biologically active amino acid sequence variants of BP53, including alleles and in vitro-generated covalent derivatives of BP53 proteins that demonstrate BP53 activity.

Amino acid sequence variants of BP53 include, for example, deletions from, or insertions or substitutions of, residues within the amino acid BP53 sequence shown in FIG. 3. Any combination of deletion, insertion and substitution may also be made to arrive at the final construct, provided that the final construct possesses the desired activity. Obviously, the mutations that will be made in the DNA encoding the variant BP53 must not place the sequence out of reading frame and preferably will not create complementary regions that could produce secondary mRNA structure (see EP 75,444A).

These variants ordinarily are prepared by site-directed mutagenesis of nucleotides in the DNA encoding the BP53, thereby producing DNA encoding the variant, and thereafter expressing the DNA in recombinant cell culture. However, variant BP53 fragments having up to about 100-150 residues may be conveniently prepared by in vitro synthesis. The variants typically exhibit the same qualitative biological activity as the naturally occurring analog.

While the site for introducing an amino acid sequence variation is predetermined, the mutation per se need not be predetermined. For example, to optimize the performance of a mutation at a given site, random mutagenesis may be conducted at the target codon or region and the expressed BP53 variants screened for the optimal combination of desired activity. Techniques for making substitution mutations at predetermined sites in DNA having a known sequence are well known, for example, M13 primer mutagenesis.

Amino acid sequence deletions generally range from about 1 to 30 residues, more preferably 1 to 10 residues, and typically are contiguous.

Amino acid sequence insertions include amino- and-/or carboxyl-terminal fusions of from one residue to polypeptides of essentially unrestricted length, as well as intrasequence insertions of single or multiple amino acid residues. Intrasequence insertions (i.e., insertions within the mature BP53 sequence) may range generally from about 1 to 10 residues, more preferably 1 to 5. An example of a single terminal insertion is mature BP53 having an N-terminal methionyl residue. This variant is an artifact of the direct expression of BP53 in recombinant cell culture, i.e., expression without a signal sequence to direct the secretion or cell membrane association of mature BP53. Other examples of terminal insertions include: (1) fusions of signal sequences, whether heterologous or homologous, to the N-terminus of mature BP53 to facilitate the secretion of mature BP53 from recombinant hosts, (2) fusions of immunogenic polypeptides (i.e., polypeptides sufficiently large to confer immunogenicity to the target sequence), e.g., bacterial polypeptides such as beta-lactamase, beta-galactosidase, or an enzyme encoded by the E. coli trp locus, and (3) fusions with cell surface binding substances, such as membrane anchors.

Fusions with cell surface binding substances need not be produced by recombinant methods, but can be the product of covalent or non-covalent association with BP53. For example, a transmembrane domain from the normal cell surface receptor for IGF-I or IGF-II, or the phospholipid anchor domain at the C-terminus of mature decay accelerating factor (mDAF) described in EPO Pub. No. 244,267 published Nov. 4, 1987, the disclosure of which is incorporated herein by reference, may be covalently bound to, or expressed in recombinant cell culture as a fusion with, the C-terminus of BP53. Thus, the BP-53 may be expressed in recombinant cell culture as a C-terminal fusion of the pre-BP53 with mDAF. For example, a fusion protein may be constructed in which the last 37 amino acids of membrane DAF predicted by the spliced cDNA is fused in-frame to the C-terminus of preBP53 glycoprotein that ordinarily is constitutively secreted to the culture medium. Rather than being secreted, this fusion construct will be transported to the cell membrane and remain lodged there by virtue of the phosphatidycholine anchor.

The third group of variants are those in which at least one amino acid residue in the BP53 molecule, and preferably only one, has been removed and a different residue inserted in its place. Such substitutions generally are made in accordance with the following Table 1 when it is desired to modulate finely the characteristics of BP53.

TABLE 1

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in BP53 properties will be those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine or proline residue is substituted for (or by) any other residue; (d) a residue having an electropositive side chain, e.g., lysyl, arginyl, or histidyl, is substituted for (or by) an electronegative residue, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the BP53 molecule. However, when it is difficult to predict the exact effect of the substitution, deletion, or insertion in advance of doing so, for example, when modifying the IGF binding domain or an immune epitope, one skilled in the art will appreciate that the effect will be evaluated by routine screening assays. For example, a variant typically is made by site-specific mutagenesis of the native BP53-encoding nucleic acid, expression of the variant nucleic acid in recombinant cell culture, and, optionally, purification from the cell culture, for example, by immunoaffinity adsorption on a rabbit polyclonal anti-BP53 column (to absorb the variant by at least one remaining immune epitope). The activity of the cell lysate or purified BP53 variant is then screened in a suitable screening assay for the desired characteristic. For example, a change in the immunological character of the BP53, such as affinity for a given antibody, is measured by a competitive-type immunoassay. Changes in immunomodulator activity are measured by the appropriate assay. Modifications of such protein properties as redox or thermal stability, hydrophobicity, susceptibility to proteolytic degradation, or the tendency to aggregate with carriers or into multimers are assayed by methods well known to the ordinarily skilled artisan.

DNA encoding BP53 may be obtained from other sources than human by (a) obtaining a cDNA library from tissues expressing BP53 mRNA of the particular mammal, (b) conducting hybridization analysis with labeled DNA encoding human BP53 or fragments thereof (usually greater than 100 base pairs in length) to detect clones in the cDNA library containing homologous sequences, and (c) analyzing the clones by restriction enzyme analysis and nucleic acid sequencing to identify full-length clones. If full-length clones are not present in the library, then appropriate fragments may be recovered from the various clones using the nucleic acid sequence information disclosed herein for the first time and ligated at restriction sites common to the clones to assemble a full-length clone encoding BP53. Alternatively, genomic libraries will provide the desired DNA.

BP53 may be made by any technique, including both synthetic and recombinant methods. Likewise, an isolated DNA is understood herein to mean chemically synthesized DNA, cDNA, chromosomal, or extrachromosomal DNA with or without the 3' and/or 5' flanking regions. Preferably, the BP53 herein is made by synthesis in recombinant cell culture. For such synthesis, it is first necessary to secure nucleic acid that encodes BP53. The inventors encountered considerable hardship in attempting to identify any nucleic acid encoding BP53 from a human cDNA library. The sequence of the human DNA encoding BP53 that was ultimately determined is shown in FIG. 3. One reproducing the process now would not have these problems because perfectly complementary probes can be obtained from the sequence in FIG. 3. Once this DNA has been identified, using hybridization of several synthetic probes, the DNA isolated from the library is ligated into a replicable vector for further cloning or for expression.

For sequence determination, native BP53 is obtained from mammalian plasma and purified generally from the Cohn IV fraction thereof. Most commonly, the procedure used to isolate and purify the native BP53 is described in Martin and Baxter, *J. Biol. Chem.*, 261: 8754–8760 (1986), the disclosure of which is incorporated herein by reference. Briefly, the Cohn paste is blended with acetic acid, NaCl solution and the resulting homogenate is centrifuged for 30 min. at 4200 rpm. Endogenous IGF is removed by stirring the supernatant with SP-Sephadex C-25 equilibrated with homogenizing buffer adjusted to pH 3.0. After 72 hours the stirring is stopped, the gel allowed to settle out, and the supernatant carefully decanted. The supernatant is then adjusted to pH 4, resulting in a precipitate removed by centrifugation. The resulting supernatant is then adjusted to pH 6.5 and the mixture again centrifuged. The resulting supernatant is pumped onto a carefully prepared affinity column of agarose-IGF-II. The column is then washed with sodium phosphate buffer at pH 6.5. The protein is eluted with acetic acid, pH 3.0 at 1 ml/min. Active fractions are combined and applied to a reverse-phase high performance liquid chromatography column equilibrated with 15% acetonitrile in 0.1% trifluoroacetic acid. A linear gradient to 60% acetonitrile is immediately commenced and is for 30 minutes at 1.5 ml./min. A single peak of the protein is obtained.

In one example of a recombinant expression system BP53 is expressed in prokaryotes, which do not process and secrete mature protein, by transforming with an expression vector comprising DNA encoding BP53. It is preferable to transform host cells capable of accomplishing such processing so as to obtain BP53 in the culture medium or periplasm of the host cell. Typically, higher eukaryotic host cells such as mammalian cells are capable of processing BP53 and secreting mature BP53 upon transformation with DNA encoding BP53.

Secreted mature BP53 can be obtained by ligating the 5' end of the DNA encoding mature BP53 to the 3' end of DNA encoding a signal sequence recognized by the host cell. An expression vector comprising the ligated DNA sequences is used to transform host cells. The host cell will process the expressed fusion by proteolytically cleaving the peptide bond between the signal sequence and the first amino acid of BP53 and secreting the mature BP53 into the host cell periplasm or into the medium, depending upon the host cell in question. For example, in the construction of a prokaryotic expression vector the BP53 secretory leader, i.e., amino acids −27 to −1, is replaced by the bacterial alkaline phosphatase or heat-stable enterotoxin II leaders, and for yeast the BP53 leader is replaced by the yeast invertase, α-factor, or acid phosphatase leaders. Gram-negative organisms transformed with a homologous signal-BP53 fusion will secrete mature BP53 into the cell periplasm, whereas yeast or Bacillus sp. will secrete mature BP53 into the culture medium.

Vectors are useful for performing two functions in collaboration with compatible host cells (a host-vector system). One function is to facilitate the cloning of the nucleic acid that encodes the BP53, i.e., to produce usable quantities of the nucleic acid. The other function is to direct the expression of BP53. One or both of these functions are performed by the vector-host system. The vectors will contain different components depending on the function they are to perform as well as the host cell that is selected for cloning or expression.

Each vector will contain nucleic acid that encodes BP53 as described above. Typically, this will be DNA that encodes the BP53 in its mature form linked at its amino terminus to a secretion signal. This secretion signal preferably is the BP53 presequence that normally directs the secretion of BP53 from human cells in vivo. However, suitable secretion signals also include signals from BP53 of other animals, viral signals, or signals from secreted polypeptides of the same or related species.

Expression and cloning vectors contain a nucleic acid sequence that enables the vector to replicate in one or more selected host cells. Generally, in cloning vectors this sequence is one that enables the vector to replicate independently of the host chromosomes, and includes origins of replication or autonomously replicating sequences. Such sequences are well known for a variety of bacteria, yeast and viruses. The origin of replication from the well known plasmid pBR322 (Bolivar et al., *Gene*, 2: 95-113 (1977)) is suitable for most Gram-negative bacteria; the 2μ plasmid origin for yeast and various viral origins (SV40, polyoma, adenovirus, VSV, or BPV) are useful for cloning vectors in mammalian cells. Origins are not needed for mammalian expression vectors (the SV40 origin is used in the examples only because it contains the early promoter). Most expression vectors are "shuttle" vectors, i.e., they are capable of replication in at least one class of organisms, but can be transfected into another organism for expression. For example, a vector is cloned in *E. coli* and then the same vector is transfected into yeast or mammalian cells for expression, even though it is not capable of replicating independently of the host cell chromosome.

DNA also may be cloned by insertion into the host genome. This cloning may be accomplished with bacillus species, for example, by including in a vector a DNA sequence that is complementary to a sequence found in bacillus genomic DNA. Transfection of bacillus with this vector results in homologous recombination with the genome and insertion of BP53 DNA. However, the recovery of genomic DNA encoding BP53 is more complex than that of an exogenously replicated vector because restriction enzyme digestion is required to excise the BP53 DNA. Generally, DNA is inserted into a host genome for purposes of preparing a stable cell line or microbe for BP53 expression.

Expression and cloning vectors should contain a selection gene, also termed a selectable marker. This is a gene that encodes a protein necessary for the survival or growth of a host cell transformed with the vector. The presence of this gene ensures that any host cell that deletes the vector will not obtain an advantage in growth or reproduction over transformed hosts. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for bacilli.

A suitable selection gene for use in yeast is the trp1 gene present in the yeast plasmid YRp7 (Stinchcomb et al. (1979) *Nature*, 282: 39; Kingsman et al. (1979) *Gene*, 7: 141; or Tschemper et al. (1980) *Gene*, 10: 157). The trp1 gene provides a selection marker for a mutant strain of yeast lacking the ability to grow in tryptophan, for example, ATCC No. 44,076 or PEP4-1 (Jones (1977) *Genetics*, 85: 12). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

Examples of suitable selectable markers for mammalian cells are dihydrofolate reductase (DHFR) or thymidine kinase. Such markers enable the identification of cells that were competent to take up the BP53 nucleic acid. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes BP53. Amplification is the process by which genes in greater demand for the production of a protein critical for growth are reiterated in tandem within the chromosomes of successive generations of recombinant cells. Increased quantities of BP53 are synthesized from the amplified DNA.

For example, cells transformed with the DHFR selection gene are first identified by culturing all of the transformants in a culture medium that lacks hypoxanthine, glycine, and thymidine. An appropriate host cell in this case is the Chinese hamster ovary (CHO) cell line deficient in DHFR activity, prepared and propagated as described by Urlaub and Chasin (1980) *Proc. Nat'l. Acad. Sci.* (USA) 77: 4216. A particularly useful DHFR is a mutant DHFR that is highly resistant to MTX (EP 117,060A). This selection agent can be used with any otherwise suitable host, e.g., ATCC No. CCL61 CHO-K1), notwithstanding the presence of endogenous DHFR. The DHFR- and BP53-encoding DNA then is amplified by exposure to an agent (methotrexate, or MTX) that inactivates the DHFR. One ensures that the cell requires more DHFR (and consequently amplifies all exogenous DNA) by selecting only for cells that can grow in successive rounds of ever-greater MTX concentration.

Expression vectors, unlike cloning vectors, should contain a promoter that is recognized by the host organism and is operably linked to the BP53 nucleic acid. Promoters are untranslated sequences located upstream from the start codon of a structural gene (generally within about 100 to 1000 bp) that control the transcription and translation of nucleic acid sequences under their control. They typically fall into two classes, inducible and constitutive. Inducible promoters are promoters that initiate increased levels of transcription from DNA under their control in response to some change in culture conditions, e.g., the presence or absence of a nutrient or a change in temperature. Constitutive promoters are not induced by changes in culture conditions. At this time a large number of promoters recognized by a variety of potential host cells are well known. These promoters may be operably linked to BP53-encoding DNA by removing them from their gene of origin by restriction enzyme digestion, and then inserting them 5' to the start codon for BP53. This is not to say that the genomic BP53 promoter is not usable. However, promoters heterologous to BP53 generally will result in greater transcription and higher yields of expressed BP53.

Promoters suitable for use with prokaryotic hosts include the β-lactamase and lactose promoter systems (Chang et al., Nature, 275:615 (1978) and Goeddel et al., Nature, 281: 544 (1979)), alkaline phosphatase, a tryptophan (trp) promoter system (Goeddel, Nucleic Acids Res., 8: 4057 (1980) and EPO Appln. Publ. No. 36,776), and hybrid promoters such as the tac promoter (H. de Boer et al., Proc. Nat'l. Acad. Sci. (USA) 80: 21-25 (1983)). However, other known bacterial promoters are suitable. Their nucleotide sequences have been published, thereby enabling a skilled worker operably to ligate them to DNA encoding BP53 (Siebenlist et al., Cell, 20: 269 (1980)) using linkers or adapters to supply any required restriction sites (Siebenlist et al, Cell, 20: 269 (1980)). Promoters for use in bacterial systems also will contain a Shine-Dalgarno (SD) sequence operably linked to the DNA encoding BP53.

Suitable promoting sequences for use with yeast hosts include the promoters for 3-phosphoglycerate kinase (Hitzeman et al., J. Biol. Chem., 255: 2073 (1980)) or other glycolytic enzymes (Hess et al., J. Adv. Enzyme Reg., 7: 149 (1968) and Holland, Biochemistry, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters that are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization (Holland, op cit.). Suitable vectors and promoters for use in yeast expression are further described in R. Hitzeman et al., EP 73,657A. Yeast enhancers also are advantageously used with yeast promoters.

BP53 transcription from vectors in mammalian host cells is controlled by promoters obtained from various sources, for example, the genomes of viruses such as polyoma, Simian Virus 40 (SV40), adenovirus, retroviruses, hepatitis-B virus, and, most preferably, cytomegalovirus, or from heterologous mammalian promoters, e.g., beta actin promoter. The early and late promoters of the SV40 virus are conveniently obtained as an SV40 restriction fragment that also contains the SV40 viral origin of replication (Fiers et al., Nature, 273: 113 (1978)). The immediate early promoter of the human cytomegalovirus is conveniently obtained as a HindIII E restriction fragment (Greenaway, P. J. et al., Gene, 18: 355-360 (1982)). Of course, promoters from the host cell or related species also are useful herein.

Transcription of BP53-encoding DNA by higher eukaryotes is increased by inserting an enhancer sequence into the vector. Enhancers are cis-acting elements of DNA, usually from about 10 to 300 bp, that act on a promoter to increase its transcription initiation capability. Enhancers are relatively orientation and position independent, having been found 5' (Laimins, L. et al., Proc. Natl. Acad. Sci., 78: 993 (1981)) and 3' (Lusky, M. L., et al., Mol. Cell Bio., 3: 1108 (1983)) to the transcription unit, within an intron (Banerji, J. L. et al., Cell, 33: 729 (1983)) as well as within the coding sequence itself (Osborne, T. F., et al., Mol. Cell Bio., 4: 1293 (1984)). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer on the late side of the replication origin, and adenoviral enhancers. The enhancers may be spliced into the vector at a position 5' or 3' to the BP53-encoding sequence, but is preferably located at a site 5' from the promoter.

Expression vectors used in eukaryotic host cells (yeast, fungi, insect, plant, animal, human, or nucleated cells) may also contain sequences necessary for the termination of transcription that may affect mRNA expression. These regions are transcribed as polyadenylated segments in the untranslated portion of the mRNA encoding BP53. The 3' untranslated regions also include transcription termination sites.

Other vectors suitable for adaptation to the synthesis of heterologous proteins in recombinant vertebrate cell culture are described in M. J. Gething et al., Nature, 293: 620-625 (1981); N. Mantei et al., Nature, 281: 40-46; and A. Levinson et al., EP 117,060A and 117,058A. A particularly useful starting plasmid for mammalian cell culture expression of BP53 is pUC118, described by Vieira and Messing, Meth. Enzymol., 153: 3-11 (1987), the disclosure of which is incorporated herein by reference. Briefly, pUC118 is a 3.2 kb plasmid with ampicillin resistance and M13 IG region, and a sequence encoding the lacZ peptide containing unique restriction sites for cloning. pUC118 is pUC18 (described by Norrander et al., Gene, 26: 101 (1983)) with the IG region of M13 from the HgiAI site (5465) to the DraI site (5941) inserted at the unique NdeI site (2499)

of pUC. The orientation of the M13 IG region is such that the strand of the lac region that is packaged as ssDNA is the same as in the M13mp vectors.

Suitable host cells for cloning or expressing the vectors herein are prokaryotes, yeast, or higher eukaryotic cells. Prokaryotes include Gram-negative or Gram-positive organisms, for example, *E. coli* or bacilli. A preferred cloning host is *E. coli* 294 (ATCC No. 31,446), although other Gram-negative or Gram-positive prokaryotes such as *E. coli* B, *E. coli* X1776 (ATCC No. 31,537), *E. coli* W3110 (F−, λ−, prototrophic, ATCC No. 27,325), bacilli such as *Bacillus subtilus, Salmonella tryphimurium,* Pseudomonas species, or *Serratia Marcesans* are suitable. If a prokaryotic cell is employed as host for expression, preferably the expression vector contains a signal sequence for transport of the protein into the culture medium. Otherwise, the protein, which contains 18 cysteine residues, will be produced in the form of refractile bodies that require special treatment to recover the protein, which treatment involves refolding of the protein.

In addition to prokaryotes, eukaryotic microbes such as filamentous fungi or yeast are suitable hosts for BP53-encoding vectors. *Saccharomyces cerevisiae*, or common baker's yeast, is the most commonly used eukaryotic microorganism, although a number of other strains are commonly available. For expression in Saccharomyces, the plasmid YRp7 (Stinchcomb, et al., *Nature,* 282: 39 (1979); Kingsman et al., *Gene,* 7: 141 (1979); Tschemper et al., *Gene,* 10: 157 (1980)) is commonly used. This plasmid already contains the trp1 gene that provides a selection marker for a mutant strain of yeast lacking the ability to grow in tryptophan, for example, ATCC No. 44,076 or PEP4-1 (Jones, *Genetics,* 85: 12 (1977)). The presence of the trp1 lesion as a characteristic of the yeast host cell genome then provides an effective means of selection by growth in the absence of tryptophan.

The preferred host cells for the expression of BP53 are cells derived from multicellular organisms. As described above, the large number of cysteine residues on BP53 suggest that the host cell will optimally be of a higher phylogenetic order than the prokaryotes if one is to expect the recombinant protein to demonstrate optimal conformational fidelity to native BP53. It also may be necessary to ensure glycosylation of BP53. All of these functions can be performed best by higher eukaryotic cells. In principle, any higher eukaryotic cell culture is workable, whether from vertebrate or invertebrate culture, although cells from mammals such as monkeys, rats, hamsters, and humans are preferred. Propagation of such cells in culture is per se well known. See *Tissue Culture,* Academic Press, Kruse and Patterson, editors (1973). Examples of useful mammalian host cell lines include monkey kidney CV1 line transformed by SV40 (COS-7, ATCC CRL 1651); human embryonic kidney cell line 293 (Graham, F. L. et al., *J. Gen. Virol.,* 36: 59 (1977)); baby hamster kidney cells (BHK, ATCC CCL 10); Chinese hamster ovary cells-DHFR (CHO, Urlaub and Chasin, *Proc. Natl. Acad. Sci.* (USA) 77: 4216 (1980)); mouse sertoli cells (TM4, Mather, J. P., *Biol. Reprod.,* 23: 243-251 (1980)); monkey kidney cells (CV1, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CC1 51), and TRI cells (Mather, J. P. et al., *Annals N.Y. Acad. Sci.,* 383: 44-68 (1982)).

Construction of suitable vectors containing the desired coding and control sequences employs standard ligation techniques. Isolated plasmids or DNA fragments are cleaved, tailored, and religated in the form desired to form the plasmids required.

For analysis to confirm correct sequences in plasmids constructed, the ligation mixtures are used to transform *E. coli* K12 strain 294 (ATCC 31,446) or other suitable host. Successful transformants are selected by ampicillin, tetracycline, or other antibiotic resistance, or by using other markers depending on the mode of plasmid construction, where appropriate. Plasmids from the transformants may then be prepared according to the method of Clewell, D. B., et al., *Proc. Natl. Acad. Sci.* (USA) 62: 1159 (1969), optionally following chloramphenicol amplification (Clewell, D. B., *J. Bacteriol.,* 110: 667 (1972)). The isolated DNA is analyzed by restriction and/or sequenced by the dideoxy method of Messing et al., *Nucleic Acids Res.,* 9: 309 (1981) or by the method of Maxam et al., *Methods in Enzymology,* 65: 499 (1980).

Host cells can be transformed with the expression vectors of this invention and cultured in conventional nutrient media modified as is appropriate for inducing promoters, selecting transformants, or amplifying genes. The culture conditions, such as temperature, pH and the like, suitably are those previously used with the host cell selected for cloning or expression, as the case may be, and will be apparent to the ordinarily skilled artisan.

BP53 preferably is recovered from the culture medium or periplasm as a secreted protein. It also may be recovered from host cell lysates when directly expressed without a secretory signal where as a first step the culture medium or lysate is centrifuged to remove particulate cell debris. BP53 also may be purified from contaminant soluble proteins, for example, by adsorption on a selection column such as ConA and elution therefrom, or adsorption on an anti-BP53 immunoaffinity column and elution therefrom. Alternatively, other processes such as chromatography on alkyl Sepharose, silica, or an anion or cation exchange resin or gel electrophoresis may be used to separate the BP53 from contaminants. BP53 variants in which a membrane anchor is attached to the BP53 protein may be recovered in the same fashion as BP53.

A minor amount of a nonionic surfactant such as Tween or polyethylene glycol may be added to the BP53 during purification for stabilization purposes if necessary. A protease inhibitor such as PMSF also may be useful to inhibit proteolytic degradation during purification, and antibiotics may be included to prevent the growth of adventitious contaminants.

One skilled in the art will appreciate that purification methods suitable for native BP53 may require modification to account for changes in the character of BP53 or its variants upon expression in recombinant cell culture. For example, a BP53 polypeptide produced in prokaryotic cell culture will not adsorb to Con-A Sepharose because it will be unglycosylated. In this case, other methods such as gel electrophoresis, ion exchange, or immunoaffinity purification should be employed. Appropriate purification methods will be apparent to the ordinarily skilled practitioner, depending upon the characteristics of the particular recombinant BP53 under consideration.

For simplification of the examples and claims, certain frequently occurring terms and methods will be referenced by shorthand phrases.

"Transfection" refers to the taking up of an expression vector by a host cell whether or not any coding sequences are in fact expressed. Numerous methods of transfection are known to the ordinarily skilled artisan, for example, CaPO$_4$ and electroporation. If prokaryotic cells or cells that contain substantial cell wall constructions are used, the preferred method of transfection is calcium treatment using calcium chloride as described by Cohen, F. N. et al., *Proc. Natl. Acad. Sci.* (USA) 69: 2110 (1972). Successful transfection is generally recognized when any indication of the operation of this vector occurs within the host cell.

"Transformation" means introducing DNA into an organism so that the DNA is replicable, either as an extrachromosomal element or by chromosomal integration. Depending on the host cell used, transformation is done using standard techniques appropriate to such cells. The calcium treatment employing calcium chloride, as described by Cohen, S. N. *Proc. Natl. Acad. Sci.* (USA), 69: 2110 (1972), is generally used for prokaryotes or other cells that contain substantial cell-wall barriers. For mammalian cells without such cell walls, the calcium phosphate precipitation method of Graham, F. and van der Eb, A., *Virology*, 52: 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, P., et al., *J. Bact.*, 130: 946 (1977) and Hsiao, C. L., et al., *Proc. Natl. Acad. Sci.* (USA) 76: 3829 (1979). However, other methods for introducing DNA into cells such as by nuclear injection or by protoplast fusion may also be used.

As used herein, the expression "hybridize under stringent conditions" to describe certain DNA sequences encompassed within the scope of this invention refers to hybridizing in 50% formamide at 5×SSC at a temperature of 42° C. and washing the filters in 0.2×SSC at 60° C. (1×SSC is 0.15M NaCl, 0.015M sodium citrate.) These conditions are intended to exclude sequences that hybridize to the BP28 sequence.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. The plaques are hybridized with kinased synthetic primer at a temperature that permits hybridization of an exact match, but at which the mismatches with the original strand are sufficient to prevent hybridization. Plaques that hybridize with the probe are then selected and cultured, and the DNA is recovered.

"Operably linked" refers to juxtaposition such that the normal function of the components can be performed. Thus, a coding sequence "operably linked" to control sequences refers to a configuration wherein the coding sequence can be expressed under the control of these sequences and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, then synthetic oligonucleotide adaptors or linkers are used in accord with conventional practice.

"Control sequences" refers to DNA sequences necessary for the expression of an operably linked coding sequence in a particular host organism. The control sequences which are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may then also be integrated into the host chromosome.

As used herein, "cell," "cell line," and "cell culture" are used interchangeably and all such designations include progeny. Thus, "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included. Where distinct designations are intended, it will be clear from the context.

"Plasmids" are designated by a lower case p followed by an alphanumeric designation. The starting plasmids herein are commercially available, are publicly available on an unrestricted basis, or can be constructed from such available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors, and other requirements were used as would be known to the ordinarily skilled artisan, for example, following the manufacturer's directions. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about one hour at 37 degrees C. are ordinarily used, but may vary in accordance with the supplier's instructions. After digestion the reaction mixture is electrophoresed directly on a polyacrylamide gel to isolate the desired fragment.

"Dephosphorylation" refers to the removal of the terminal 5' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation are conventional (T. Maniatis et al., 1982, *Molecular Cloning: A Laboratory Manual* (New York: Cold Spring Harbor Laboratories, 1982), pp. 133-134). Reactions using BAP may be carried out in 50 mM Tris at 68 degrees C. to suppress the activity of any exonucleases that may be present in the enzyme preparations. Reactions may be run for one hour. Following the reaction the DNA fragment may be recovered by extracting the preparation with phenol/chloroform and precipitating with ethanol. Alternatively to dephosphorylation, religation can be prevented in vectors that have been double digested by additional restriction enzyme digestion of the unwanted fragments.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al. (1981) *Nucleic Acids Res*, 9:6103-6114, and D. Goeddel et al. (1980) *Nucleic Acids Res.* 8:4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern (1975) *J. Mol. Biol.* 98: 503-517, and hybridization as described by T. Maniatis et al. (1978) *Cell* 15: 687-701.

"Ligation" refers to the process of forming phosphodiester bonds between two double-stranded nucleic acid fragments (T. Maniatis et al., *Molecular Cloning: A Laboratory Manual*, op. cit, p. 146). Unless otherwise provided, ligation may be accomplished using known buffers and conditions with 10 units of T4 DNA ligase ("ligase") per 0.5 μg of approximately equimolar amounts of the DNA fragments to be ligated. "Sticky-end" ligation is ordinarily performed at 0 degrees C., whereas "blunt-end" ligation is generally performed at 14 degrees C.

"Filling" or "blunting" refers to the procedures by which the single-stranded end in the cohesive terminus of a restriction-enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2-15 μg of the target DNA in 10 mM $MgCl_2$, 1 mM dithiothreitol, 50 mM NaCl, 10 mM Tris (pH 7.5) buffer at about 37 degrees C. in the presence of 8 units of the Klenow fragment of DNA polymerase I and 250 μm of each of the four deoxynucleoside triphosphates. The incubation generally is terminated after 30 min. and the reaction mixture is subjected to phenol and chloroform extraction and ethanol precipitation.

"Preparation" of DNA from transformants means isolating plasmid DNA from microbial culture. Unless otherwise provided, the alkaline/SDS method of Maniatis et al., *Molecular Cloning: A Laboratory Manual*, op. cit., p. 90, may be used.

"Oligonucleotides" are short-length, single- or double-stranded polydeoxynucleotides that are chemically synthesized by known methods and then purified on polyacrylamide gels.

A summary of how BP53 was obtained through recombinant means follows:

1. Purified BP53 from human plasma was partially sequenced.
2. A series of oligonucleotide probes representing a single codon choice for each amino acid corresponding to the amino terminal portion of BP53 and to a number of the internal sequences of BP53 were chemically synthesized and labeled with $^{32}P$.
3. Two adult liver cDNA libraries were constructed in αλgt10 vector, one an oligo(dT)-primed library and one a randomly primed library.
4. Each library was screened with three probe pools. Each pool of probes gave from 300 to 1000 spots of varying intensity with each library. Thirty-eight of the spots were duplicated with two of the three probe pools; two spots appeared in triplicate, both from the oligo(dT)-primed library. Two of the clones identified hybridized with the three probe pools and with a fourth synthesized probe. Some of the duplicate and triplicate clones were subcloned and mapped.
5. One of the two subclones that hybridized to all four probe pools was sequenced and the complete DNA sequence of BP53 determined.
6. The full-length cDNA encoding BP53 was constructed in a plasmid and replicated. It should be appreciated that knowledge of the complete DNA sequence in FIG. 3 enables one to prepare extremely long probes having perfect homology with BP53 cDNA, thereby considerably simplifying and increasing the efficiency of probing cDNA or genomic libraries from other species, and making it possible to dispense with BP53 purification, sequencing, and the preparation of probe pools.
7. The cDNA encoding BP53 was excised from the cloning plasmid and legated into an expression vehicle that was used to transform an appropriate host cell, which was then grown in a culture to produce the desired BP53.
8. Biologically active, mature BP53 produced according to the foregoing procedure has 264 amino acid residues, of which 18 are cysteines.

The following examples are intended merely to illustrate the best mode now known for practicing the invention, but the invention is not to be considered limited thereto. All literature citations herein are expressly incorporated by reference.

EXAMPLE I

Identification of cDNA Clones Encoding BP53 And Cloning of Human Serum BP53

DNA encoding BP53 may be obtained by chemical synthesis when the complete DNA sequence is known, by screening reverse transcripts of mRNA from human liver, or by screening genomic libraries from any cell. As neither the complete amino acid nor DNA sequence of BP53 protein was known at the time of this invention, the chemical synthesis of the complete DNA sequence encoding BP53 was not possible at that time.

Human serum binding protein BP53 was purified from the Cohn Fraction IV paste of human plasma obtained from Commonwealth Serum Laboratories, Melbourne, Australia as described by Martin and Baxter, *J. Biol. Chem.*, op. cit. The single HPLC peak representing purified BP53 was isolated, and the amino acid sequences obtained from this material are shown in Table 2.

The 60-amino-acid N-terminal sequence obtained matched the 15-amino-acid sequence reported previously by Baxter and Martin, *Biochem. Biophys. Res. Comm.* 147: 408–415 (1987), except at position 5 where an alanine residue had been found previously. The current sequence gave approximately equal yields of alanine and glycine, suggesting that the currently isolated protein is a mixture with both residues at this position. After the N-terminal sequence of 60 residues was complete, the protein remaining on the sequencer filter was cleaved with cyanogen bromide, as described by Gross and Witkup, *J. Am. Chem. Soc.*, 83: 1510–1511 (1961). A clear internal sequence was then found (see Table 2, CNBr).

Trypsin and lysine-C proteolytic cleavage of the protein followed by isolation of the peptides by reverse-phase chromatography gave a unique sequence for an additional nine internal peptides and three mixture sequences. For trypsin digestion, 8.4 μg of purified BP53 was incubated with 0.5 μg trypsin in 100 μl 10 mM ammonium bicarbonate, 10 mM calcium chloride for 24 hours at 37° C. For lysine-C peptidase digestion, 6 μg of purified BP53 was incubated with 0.3 μg of lysine-C peptidase in 100 μl of 10 mM ammonium bicarbonate, 0.1% SDS, 10 mM dithiothreitol (DTT) for 24 hours at 37° C. These fragments were separated by applying the digests directly to a Sychropak 300 A C4 HPLC column (2×100 mm) followed by elution with a linear gradient of 1 to 70% acetonitrile or 1-propanol in 0.1% trifluoroacetic acid. This digestion and RP-HPLC purification technique is described more fully in Aggarwal et al., *J. Biol. Chem.*, 260: 2334–2344 (1985). Segments of the BP53 amino acid sequence were obtained using a 470A Applied Biosystems gas-phase sequencer equipped with a 120A PTH amino acid analyzer and a Nelson 300 data system, as described in Henzel et al., *Chromatography*, 404: 41–52 (1987).

TABLE 2

Amino Acid Sequence of BP53 Peptides

|  |  | Approximate Initial Yield (pmoles) | Position in the cDNA Sequence |
|---|---|---|---|
| N-terminal |  |  |  |
| N: | A G A S S G G L G P V V R C E P C D A R A L A Q C A P P P A V C A E L V R E P G(C)G(C C) L(L)X A L(C)E G Q P(P)X X X (T) (E) (R) | 185 | 1–60 |
| CNBr: | E X T L N H L K F L N V L S P R G V H I P N X D X K GF Y | 66 | 191–219 |
| Trypsin Peptides |  |  |  |
| T15-3: | A Y L L P A P P A P G[N]A S E S E E D(D) | 32 | 98–117 |
| T2-6: | S A G S V E S P S V S S T H R | 60 | 118–132 |
| T7: | F H P L H S K | 33 | 138–144 |
| T3-18: | I I I I K | 64 | 145–149 |
| T3-14: | Y K V D Y E S Q S T D T Q[N]F S S E (E) K | 35 | 159–178 |
| T2-12: | E M E D T L N H L K | 64 | 189–198 |
| T4-19: | F L N V L S P R | 129 | 199–206 |
| T2-10-8a: | G V H I P N(N)D(W)K | 18 | 207–216 |
| T2-10-8b: | E T E Y G P(Y)R | 14 | 180–187 |
| T2-2: | G F Y K | 84 | 217–220 |
| T2-20a: | G F(C)W X V D K Y G Q P L P G Y T T K | 17 | 233–251 |
| T2-20b: | G K E D V H X Y S M Q S | 16 | 252–263 |
| Lysine C-Peptides |  |  |  |
| KC-20a: | F L N V L S P R G V H I P N X D | 89 | 199–214 |
| KC-20b: | G A S S G G L G P V V X X E P X D A | 45 | 1–18 |
| KC-20c: | R E T E Y G P(Y R K)E M E D(T)L N H | 13 | 179–196 |
| KC-9: | Y G Q P L P G Y T T K | 28 | 241–251 |

Single-letter codes are employed for the amino acids, using a coding system known in the art. X indicates residues that could not be identified. Parentheses indicate uncertain residues. Brackets indicate Asn residues that gave no sequence and may therefore be glycosylated. The mixture sequences for T2-10-8, T2-20, and KC-20 were resolved with the help of the cDNA sequence.

Two human adult liver cDNA libraries in a λgt10 vector were used to screen for clones of BP53. One was a randomly primed library prepared as described by Leung et al., *Nature*, 330: 537–543 (1987). The other, a human liver oligo(dT)-primed cDNA library, was generally prepared from liver RNA using an oligo(dT)-primer that was 12 to 18 nucleotides in length and AMV reverse transcriptase. After treatment of the resulting RNA-DNA complex with DNase-free RNase-A, both the Klenow fragment of DNA polymerase I and additional AMV reverse transcriptase were used to synthesize the second DNA strand using techniques well known in the art. The double-stranded cDNA (ds-cDNA) thus prepared was digested with S1 nuclease and treated with the Klenow fragment of DNA polymerase I. The now blunt-ended ds-cDNA was ligated to a phosphorylated 16-nucleotide oligomer as well as to a non-phosphorylated 20-nucleotide oligomer containing restriction sites for SalI, SstI, and XhoI, and an EcoRI overhanging end. These oligomers had the sequences:
20 mer: 5'-AATTCTCGAGCTCGTCGACC
phosphorylated 16 mer: 5'-GGTCGACGAGCTCGAG This ligation product was inserted into the EcoRI site of λgt10 as described by an instruction sheet included in a commercially available DNA packaging kit (Stratagene; San Diego, Calif., catalogue #GT-10), with the method also being described by Maniatis et al., *Molecular Cloning: A Laboratory Manual*, op. cit.

Four pools of oligonucleotide probes representing a single codon choice for each of the N-terminal amino acid sequence and a number of the internal sequences (corresponding to both C-terminal and N-terminal regions) were synthesized. These synthetic oligomers were based on the amino acid sequence data shown in Table 2 above. The probes are illustrated, along with their match to the correct cDNA clones, in FIG. 1.

In FIG. 1, for each set the upper sequence is the amino acid sequence determined from purified BP53. The upper nucleotide sequence is that for the oligonucleotide probes (oibp.6,7,8,9, and 2) synthesized in accordance with Lathe, R., *J. Mol. Biol.*, 183: 1–12 (1985) based on the amino acid sequence data. The sequence labeled BP53 is the DNA sequence of the cloned cDNA, and the lower amino acid sequence is the translated sequence of BP53. The dots indicate DNA sequence matches between the probe and cDNA sequences.

Pool A is a pool of three overlapping oligonucleotides, oibp.6.1, 6.2, and 6.3, that are 69, 69, and 70 nucleotides in length, respectively. The oligonucleotides are based on a 60 amino acid sequence of BP53 composed of several overlapping tryptic, lysine-C, and CNBr fragments shown in Table 2. The location of these fragments is shown above the upper amino acid sequence. The two-amino-acid (Y,K) overlap of the last of the fragment, T3-14, proved to be incorrect, and this peptide is actually located elsewhere in the protein. Thus, a second lower sequence is shown under amino acids 41-60.

Pool B is a pool of two oligonucleotides, oibp.7 and 8, that are 45 and 36 nucleotides in length, respectively.

Pool C is a pool of three overlapping oligonucleotides, oibp.9.1, 9.2 and 9.3, that are 63, 63, and 64 nucleotides in length, respectively.

Pool D consists of a single oligonucleotide, oibp.2, that is 60 nucleotides in length.

These newly synthesized oligomers were labeled with $^{32}$P, and the three pools A, B and C were used to screen the human liver cDNA libraries described above.

Six-hundred thousand clones of the oligo(dT)-primed library and 600,000 clones of the randomly primed human liver cDNA library were screened in triplicate with the three pools of oligonucleotide probes. Triplicate nitrocellulose filters were hybridized with the pools of $^{32}$P-end-labeled probes. The hybridization was performed in a buffer that included 20% formamide, 10% dextran sulfate, 5×SSC, 50 mM sodium phosphate (pH6.5), 5×Denhardt's solution, 2 mM sodium pyrophosphate, 0.1% SDS, and 0.04 mg/ml boiled, sonicated salmon sperm DNA. The filters were hybridized at 420° C. overnight. After hybridization, the filters were washed twice in 1×SSC at 37° C. for two hours, as described by Maniatis et al., *Molecular Cloning: A Laboratory Manual*, op. cit.

Figure 2:
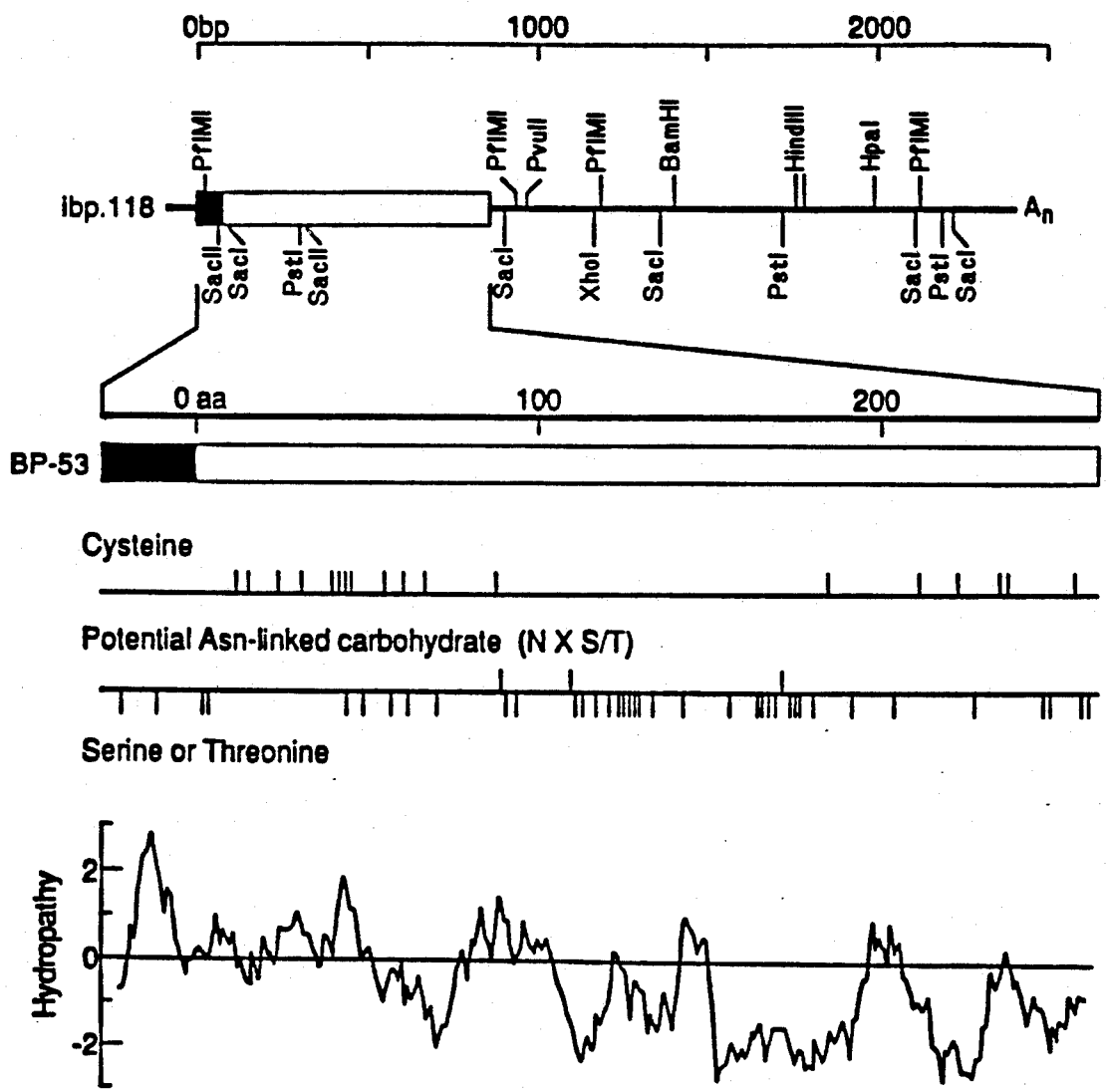
FIG. 2 depicts a diagram of the BP53 cDNA and translated amino acid sequence. The open box indicates the region encoding the mature BP53, and the filled box, the putative signal sequence. The hydropathy plot is from the method of Kyte and Doolittle, *J. Mol. Biol.,* 157:105-132 (1982) with a window of ten residues.

Each of the pools A, B and C gave 300–1000 hybridized positives of varying intensity with each library. Thirty-eight hybridizing duplicate positives were observed with two of the three pools. Two hybridizing triplicate positives were observed with the oligo(dT)-primed library, hybridizing with all four pools. A number of these duplicate and triplicate clones were plaque purified and subcloned into pUC118 (Vieira and Messing, op. cit.) vectors for DNA sequencing by dideoxy chain termination, as described by Messing et al., *Nucleic Acids Res.*, 9: 309–321 (1981). Some of the clones were mapped, and through both restriction mapping and sequence analysis, one clone, designated ibp.118, was shown to contain BP53 (FIG. 2). Included within this clone were the coding and 3'-untranslated regions of BP53 as illustrated in FIG. 3.

EXAMPLE II

DNA Sequence of BP53 cDNA

The complete nucleotide sequence of the BP53 cDNA clone is shown in FIG. 3. The sequenced clone contains a single long open reading frame of 873 bp beginning with a methionine residue. All 18 of the amino terminal and internal sequences determined from the purified protein are present in this reading frame, and in fact, about 75% of the protein sequence is represented in the peptides listed in Table 2. The amino acid sequences determined from the purified protein match exactly the deduced amino acid sequence of BP53 based on the cDNA clone, with the exception of some residues that were uncertain or could not be assigned (Table 2). The amino-terminal sequence of BP53 is preceded by a 27-amino-acid sequence beginning with a methionine. The sequence contains a hydrophobic core of 14 amino acids flanked by charged residues indicative of a secretion signal sequence, as per Perlman and Halvorson, *J. Mol. Biol.*, 167: 309 (1983). The third nucleotide 5' of the putative initiating ATG is a purine as expected from translation initiation consensus sequences (see Kozak, *Nucl. Acids Res.*, 12: 857–872 (1984)). The open reading frame is contained near the 5' end of an approximately 2500-bp messenger RNA that includes a 1500-bp 3'-untranslated region. Three of the BP-53 clones isolated (including ibp.118) contain poly(A) sequences at their 3' ends preceded by an AAATAAA poly(A) addition signal.

The full-length mature sequence of BP53 deduced from the cDNA clones is 264 residues of which 18 are cysteines, indicating that the protein is cysteine rich. The cysteine residues are clustered with 12 near the N-terminus and six near the C-terminus (see FIG. 2). The translated molecular weight of the sequence is 28.7 kD, considerably smaller than the 43 kD molecular weight determined by reduced SDS-PAGE. Presumably most or all of the molecular weight discrepancy is accounted for by glycosylation. The native protein binds the lectin Concanavalin A (Martin and Baxter, *J. Biol. Chem.*, op. cit.), and the amino acid sequence contains three potential N-linked glycosylation sites (NXS or T) as well as two clusters of serine and threonine residues (FIG. 2) that could be used for O-linked glycosylation as well (as suggested in Russell et al., *Cell*, 37: 577–585 (1984)). The lack of an asparagine signal at amino acids 109 and 172 in the amino acid sequences of peptides T15-3 and T3-14 (Table 2) suggests that at least two of the three potential N-linked glycosylation sites are utilized.

The amino acid sequence of BP53 is similar to the published sequence for an IGF-binding protein produced by rat BRL-3A cells (see Lyons and Smith, *Mol. Cell. Endo.*, 45: 263-270 (1986) and Mottola et al., *J. Biol. Chem.*, 261: 11180-11188 (1986)). The comparison is given below, where the asterisks indicate where sequence homology occurs:

```
                  10        20         30        40
BP53      GASSGGLGPVVRCEPCDARALAQCAPPP-AVCAELVREPGC
           * *  **      ** *  *** * **********  *

Rat BRL-3A protein   FRCPPCTPERLAACGPPPDAPCAELVREPGC
                     10         20        30
```

Of the 34 amino acids sequenced for the rat binding protein, 21 match the sequence of human BP53. The rat protein is believed to be the homologue of BP28, a human IGF-binding protein that is antigenically and metabolically distinct from BP53 (see Baxter et al., *J. Clin. End. and Metabol.*, op. cit., and Baxter and Martin, *Biochem. Biophys. Res. Comm.*, op. cit.). Computer-assisted searches of several protein sequence databases (Protein Identification Resource, National Biomedical Research Foundation, Georgetown Univ. Med. Center, Washington, D.C. 20007 and GenBank, Bolt, Beranek and Newman, Inc., Cambridge, Mass. 02231) show no clear similarity to any other known proteins. In particular, no similarity is found with the IGF-I and IGF-II receptor binding domains. This contrasts with recent work with the growth hormone receptor where it has been demonstrated that the extracellular hormone binding domain of the receptor is identical to a circulating growth hormone binding protein (Leung et al., *Nature*, 330: 537-543 (1987)).

EXAMPLE III

Expression of Human BP53

Figure 9:
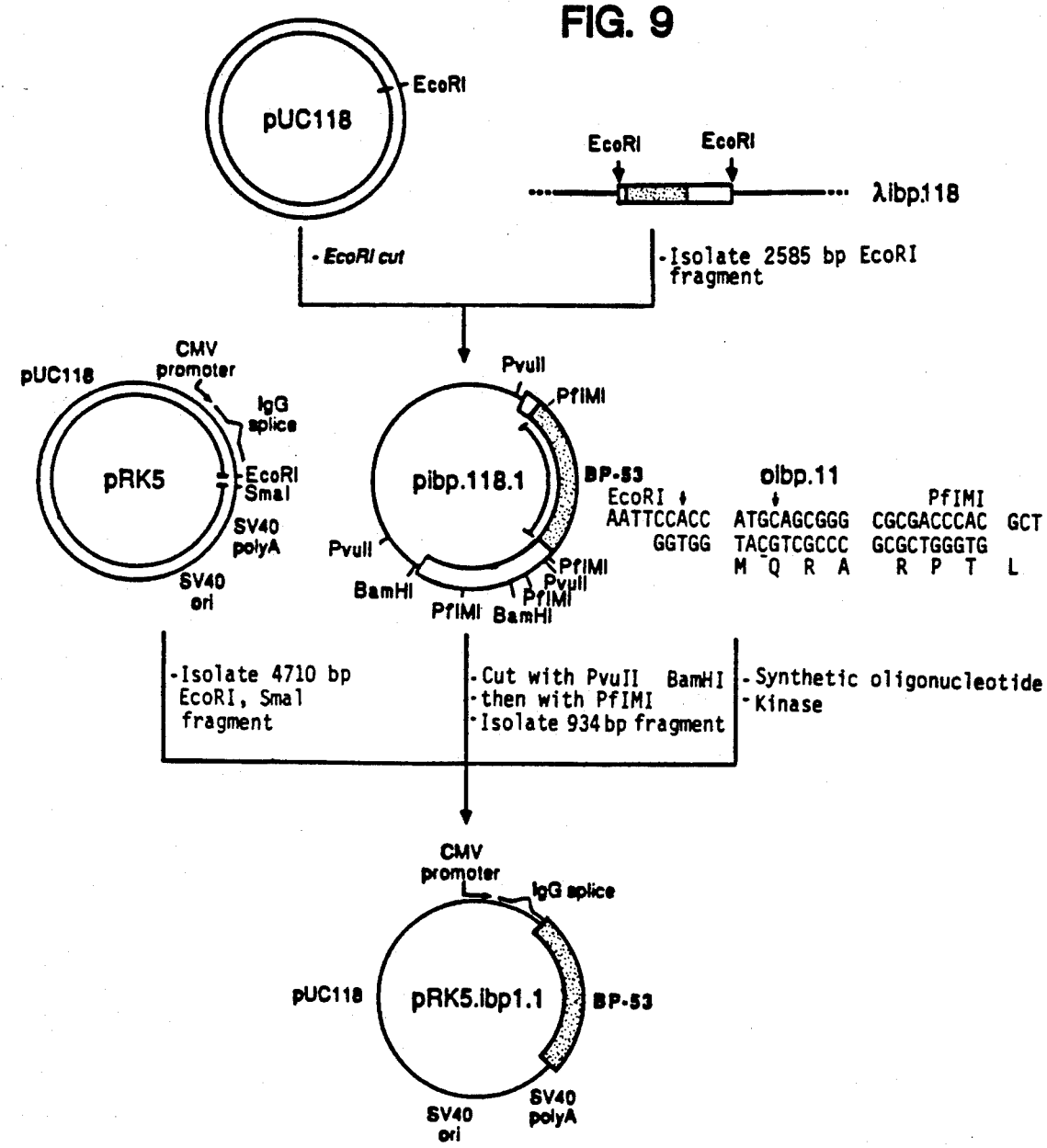
FIG. 9 depicts the construction of the expression vector pRK5.ibp1.1 used to transformed mammalian host cells to produce BP53.
Figure 10A:
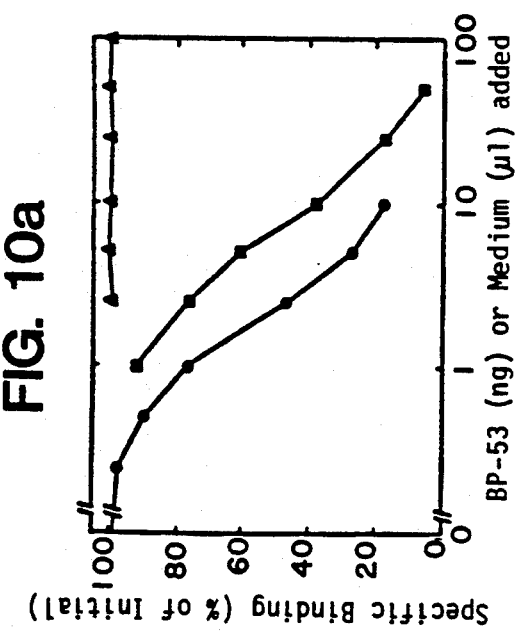
FIG. 10a is a graph of radioimmunoassay for BP53, with the circles, squares, and triangles meaning addition of purified BP53 in ng, addition of pRK5.ibp1.1-transfected culture medium in μl, and addition of control-transfected culture medium in μl, respectively.
Figure 10B:
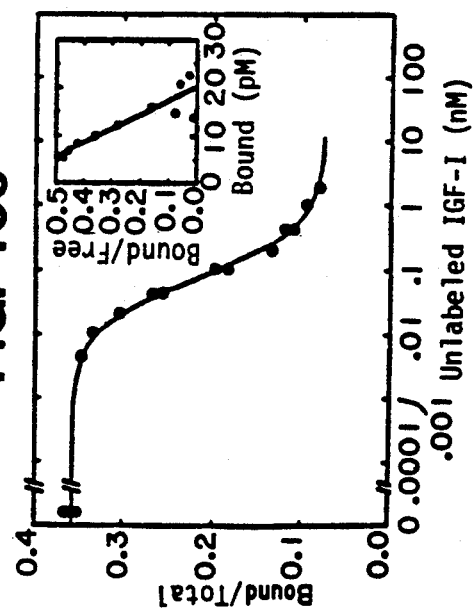
FIG. 10b depicts a graph for the binding of BP53 to labeled IGF-I (closed symbols) or IGF-II (open symbols), with the circles, squares, and triangles meaning addition of purified BP53 in ng, addition of pRK5.ibp1.1-transfected culture medium in μl, and addition of control-transfected culture medium in μl, respectively.
Figure 10C:
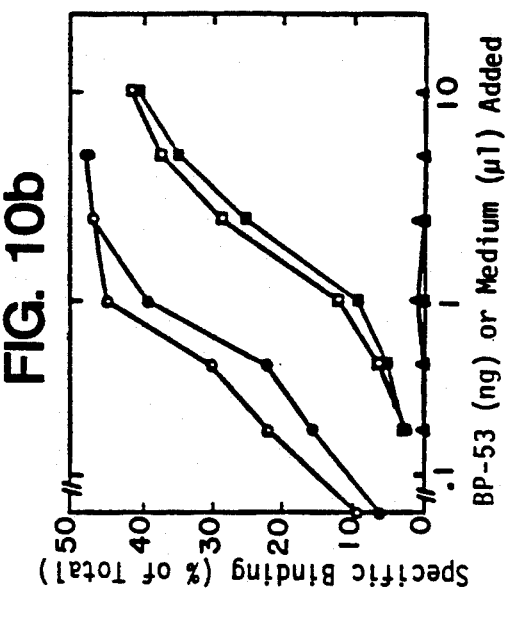
FIG. 10c depicts a graph of the competition assay with unlabeled IGF-I of the binding of labeled IGF-I to pRK5.ibp1.1-transfected culture medium. The insert is a Scatchard plot of the same data.
Figure 10D:
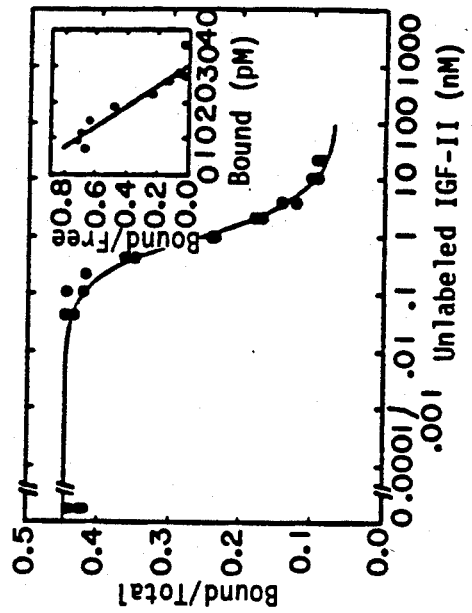
FIG. 10d depicts the same as FIG. 10c except that the binding is with IGF-II rather than IGF-I.

The final expression vector, pRK5.ibp1.1, was constructed, as shown in FIG. 9, from pibp.118.1 and pRK5. The construction of each of these plasmids, and of the final plasmid, is described below in detail.

A. Construction of pibp.118.1

The full-length human BP53 protein cDNA is contained within the clone λ ibp.118. This cDNA insert was subcloned by EcoRI digestion of λ ibp.118, isolation by agarose gel electrophoresis of the 2585 bp EcoRI fragment, and ligation using T4 ligase of this fragment into EcoRI-digested pUC118 to give plasmid pibp.118.1 (FIG. 9).

B. Construction of pRK5

B.1. Construction of pF8CIS

The initial three-part construction of the starting plasmid pF8CIS is described below and shown in FIG. 4.

1) The ampicillin resistance marker and replication origin of the final vector was derived from the starting plasmid pUC13pML, a variant of the plasmid pML (Lusky, M. and Botchen, M., *Nature*, 293: 79 [1981]). pUC13pML was constructed by transferring the polylinker of pUC13 (Vieira, J. and Messing, J., *Gene*, 19:259 (1982)) to the EcoRI and HindIII sites of pML. A second starting plasmid pUC8-CMV was the source of the CMV enhancer, promoter and splice donor sequence. pUC8-CMV was constructed by inserting approximately 800 nucleotides for the CMV enhancer, promoter and splice donor sequence into the blunted PstI and SphI sites of pUC8. Vieira, J. and Messing, J., op. cit. Synthetic BamHI-HindIII linkers (commercially available from New England Biolabs) were ligated to the cohesive BamHI end creating a HindIII site. Following this ligation a HindIII-HincII digest was performed. This digest yielded a fragment of approximately 800 bp that contained the CMV enhancer, promoter and splice donor site. Following gel isolation, this 800-bp fragment was ligated to a 2900-bp piece of pUC13pML. The fragment, required for the construction of pF8CIS, was obtained by digestion of the above intermediate plasmid with SalI and HindIII. This 3123-bp piece contained the resistance marker for ampicillin, the origin of replication from pUC13pML, and the control sequences for the CMV, including the enhancer, promoter, and splice donor site.

2) The Ig variable region intron and splice acceptor sequence was constructed using a synthetic oligomer as shown in the central portion of FIG. 4. A 99 mer and a 30 mer were chemically synthesized having the following sequence for the IgG intron and splice acceptor site (Bothwell et al., *Nature*, 290:65-67 [1981]):

```
1 5'  AGTAGCAAGCTTGACGTGTGGCAGGCTTGA...
 31   GATCTGGCCATACACTTGAGTGACAATGA...
 60   CATCCACTTTGCCTTTCTCTCCACAGGT...
 88   GTCCACTCCCAG 3'
1 3'  CAGGTGAGGGTGCAGCTTGACGTCGTCGGA 5'
```

DNA polymerase I (Klenow fragment) filled in the synthetic piece and created a double-stranded fragment. Wartell, R. M. and W. S. Reznikoff, *Gene*, 9: 307 (1980). This was followed by a double digest of PstI and HindIII. This synthetic linker was cloned into pUC13 (Veira and Messing, op. cit.) at the PstI and HindIII sites. The clone containing the synthetic oligonucleotide, labeled pUCIg.10, was digested with PstI. A ClaI site was added to this fragment by use of a PstI-ClaI linker. Following digestion with HindIII a 118-bp piece containing part of the Ig intron and the Ig variable region splice acceptor was gel isolated.

3) The third part of the construction scheme replaced the hepatitis surface antigen 3' end with the polyadenylation site and transcription termination site of the early region of SV40. A vector, pUC.SV40, containing the SV40 sequences was inserted into pUC8 at the BamHI site described by Vieira and Messing, op. cit. pUC.SV40 was then digested with EcoRI and HpaI. A 143-bp fragment containing the SV40 polyadenylation sequence was gel isolated from this digest. Two additional fragments were gel isolated following digestion of pSVE.8c1D. (European Pat. Pub. No. 160,457). The 4.8 kb fragment generated by EcoRI and ClaI digestion contains the SV40-DHFR transcription unit, the origin of replication of pML, nd the ampicillin resistance marker. The 7.5-kb fragment produced following digestion with ClaI and HpaI contains the cDNA for Factor VIII. A three-part ligation yielded pSVE.8c24D. This intermediate plasmid was digested by ClaI and SalI to give a 9611-bp fragment containing the cDNA for Factor VIII with an SV40 poly A site followed by the SV40 DHFR transcription unit.

The final three-part ligation to yield pF8CIS used: a) the 3123 bp SalI-HindIII fragment containing the origin of replication, the ampicillin resistance marker, and the CMV enhancer, promoter, and splice donor site; b) the 118-bp HindIII-ClaI fragment containing the Ig intron and splice acceptor site; and c) a 9611-bp ClaI-SalI fragment containing the cDNA for Factor VIII, the SV40 polyadenylation site, and the SV40 DHFR transcription unit.

B.2. Construction of pCIS2.8c28D pCIS2.8c28D comprises a 90-kd subunit of Factor VIII joined to a 73 kd subunit of Factor VIII. The 90-kd comprises amino acids 1 through 740 and the 73-kd subunit amino acids 1690 through 2332. This construct was prepared by a three-part ligation of the following fragments: a) the 12617-bp ClaI-SstII fragment of pF8CIS (isolated from a dam- strain and BAP treated); b) the 216-bp SstII-PstI fragment ofpF8CIS; and c) a short PstI-ClaI synthetic oligonucleotide that was kinased (see FIG. 5, where an asterisk indicates the changed nucleotide).

Figure 5:
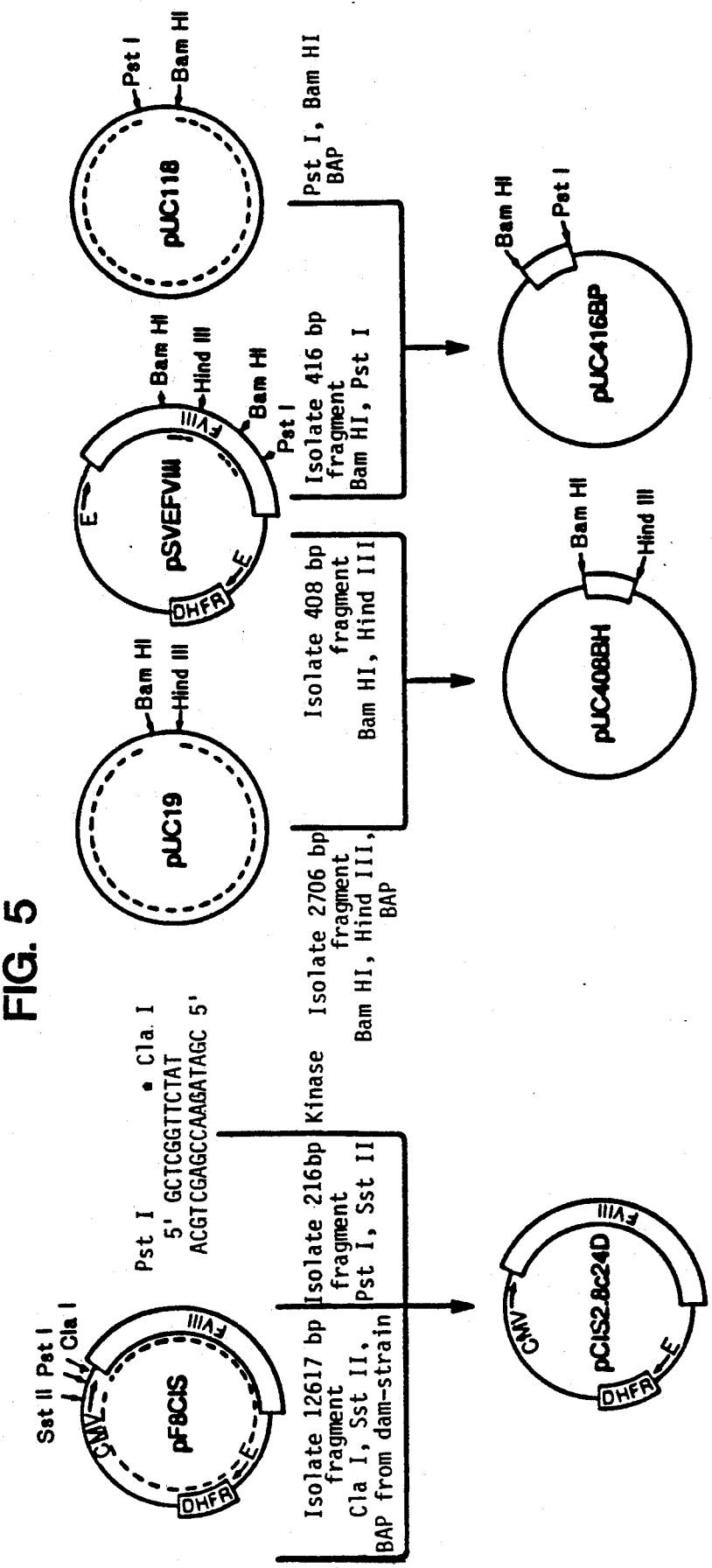
FIG. 5 depicts the construction of the intermediate vector pCIS2.8c24D for Factor VIII in which the ClaI site is not effected by dam methylation. Also shown is the subcloning of 408 and 416 bp fragments of the Factor VIII coding region for construction of a fusion plasmid.

FIG. 5 also shows the subcloning of the 408-bp BamHI-HindIII and the 416-bp BamHI-PstI fragments of pSVEFVIIII (European Pat. Publ. No. 160,457) containing the 5' and 3' DNA regions of Factor VIII to be fused to make pCIS2.8c28D.

Figure 6:
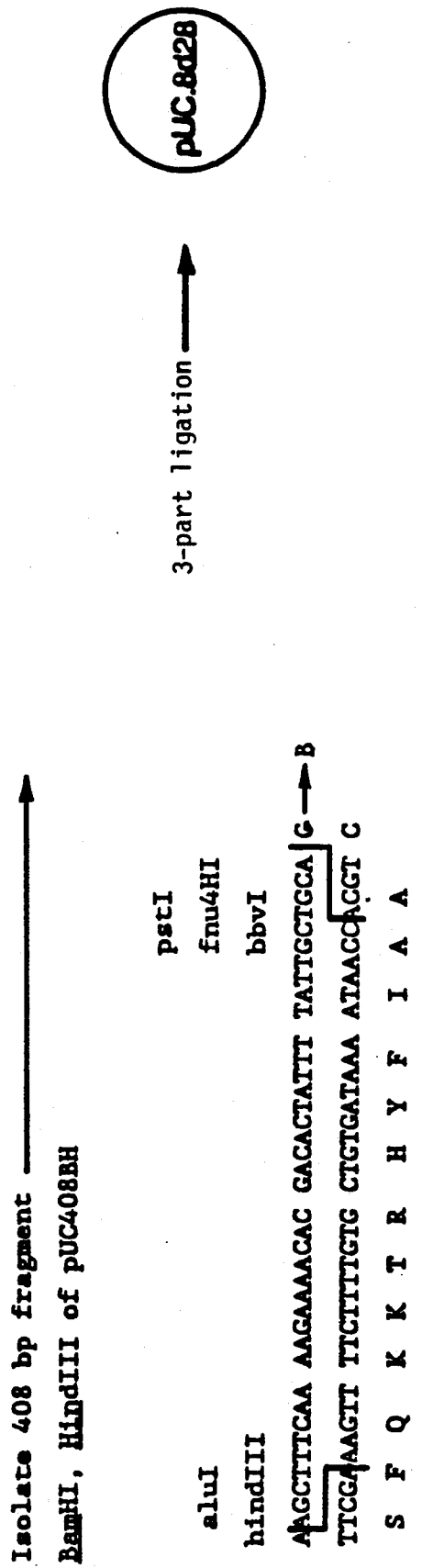
FIG. 6 depicts the construction of the intermediate plasmid pUC.8d28 containing the fusion region of a Factor VIII variant in a pUC vector.

FIG. 6 shows the three-part ligation used to construct the fusion region of pCIS2.8c28D. Two different fragments, A and B, were cloned into the same pUC118 BamHI-PstI BAP vector. The A fragment was the 408 bp BamHI-HindIII fragment of pUC408BH and the B fragment was a HindIII-PstI oligonucleotide. The double-stranded oligonucleotide is shown in FIG. 6. While complete DNA sequence at the terminal restriction sites is given in FIG. 6, the actual oligonucleotide does not include the bases delineated by the lines at the restriction sites. This oligonucleotide was used without kinasing to prevent its polymerization during ligation.

After ligation of the A and B fragments into the vector as shown in FIG. 6, the expected junction sequences were confirmed by DNA sequencing of the regions encompassed by the nucleotides.

Figure 7:
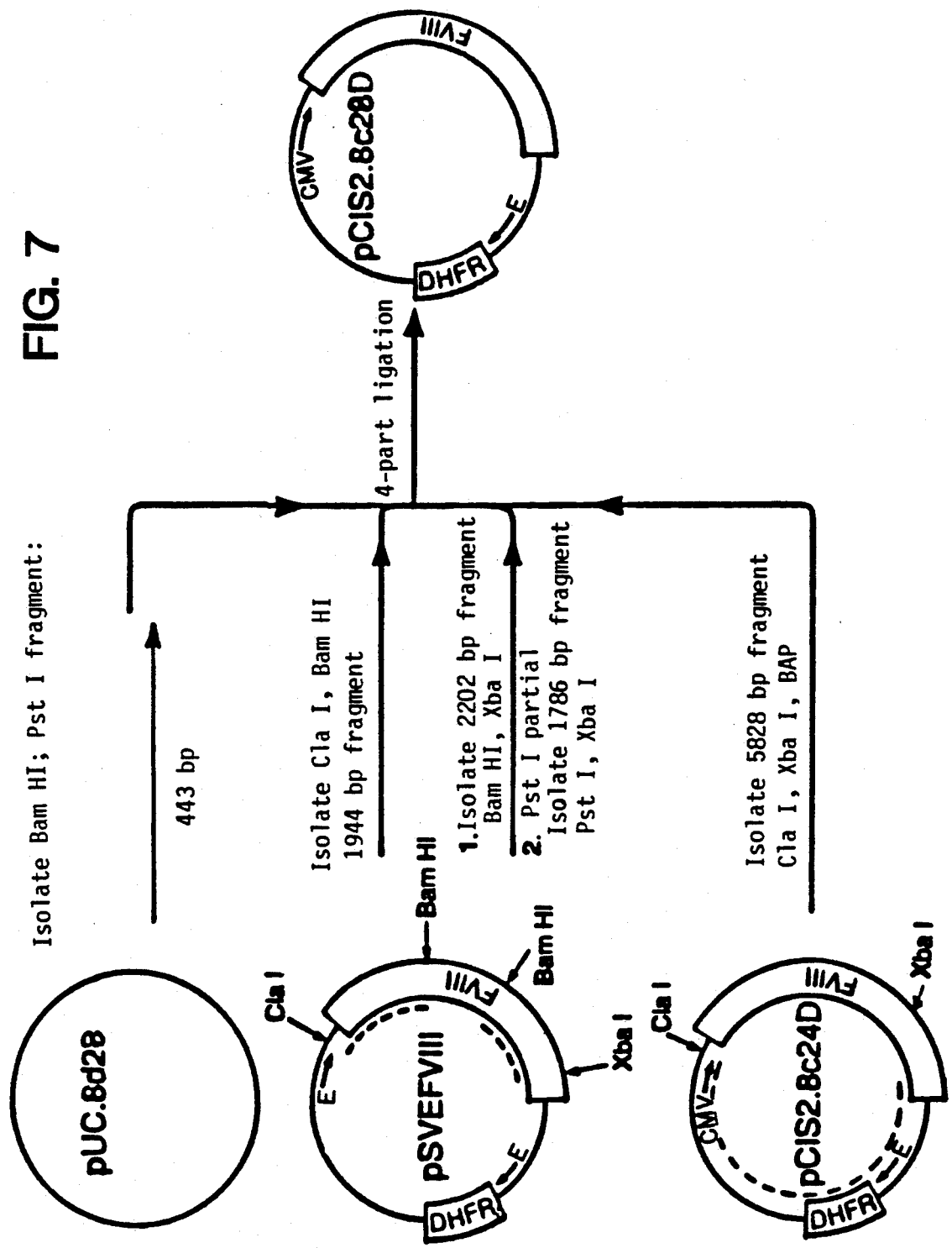
FIG. 7 depicts the construction of the intermediate expression vector encoding a Factor VIII variant protein pCIS2.8c28D.

The resulting plasmid, pCIS2.8c28D, was constructed as shown in FIG. 7, with a four-part ligation. The fusion plasmid from FIG. 6 was cut with BamHI and PstI and the 443-bp fragment isolated. The remaining three fragments of the four-part ligation were: 1) 1944-bp ClaI-BamHI fragment of pSVEFVIII (European Pat. Publ. No. 160,457); 2) a 2202-bp BamHI-XbaI fragment of pSVEFVIII, which was further partially digested with PstI and the resulting 1786 bp PstI-XbaI fragment isolated, and 3) the 5828-bp XbaI-ClaI BAP fragment of pCIS2.8c24D from FIG. 6. The translated DNA sequence of the resultant variant in the exact fusion junction region of pCIS2.8c28D was determined and correlates with the sequence shown in FIG. 6.

B.3. Construction of pRK5

Figure 8:
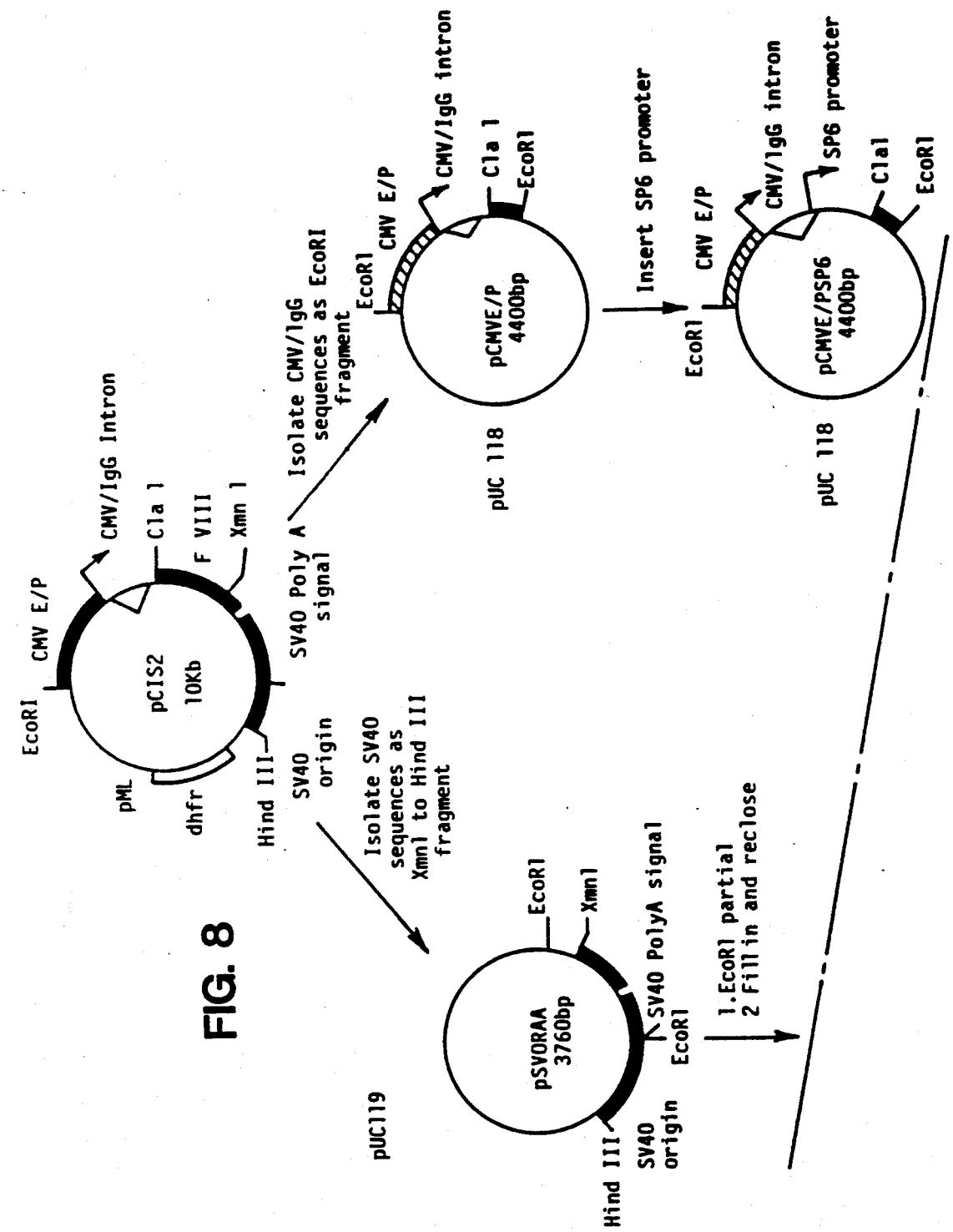
FIG. 8 depicts the construction of the expression vector pRK5 into which the DNA encoding BP53 was inserted.
Figure 8:
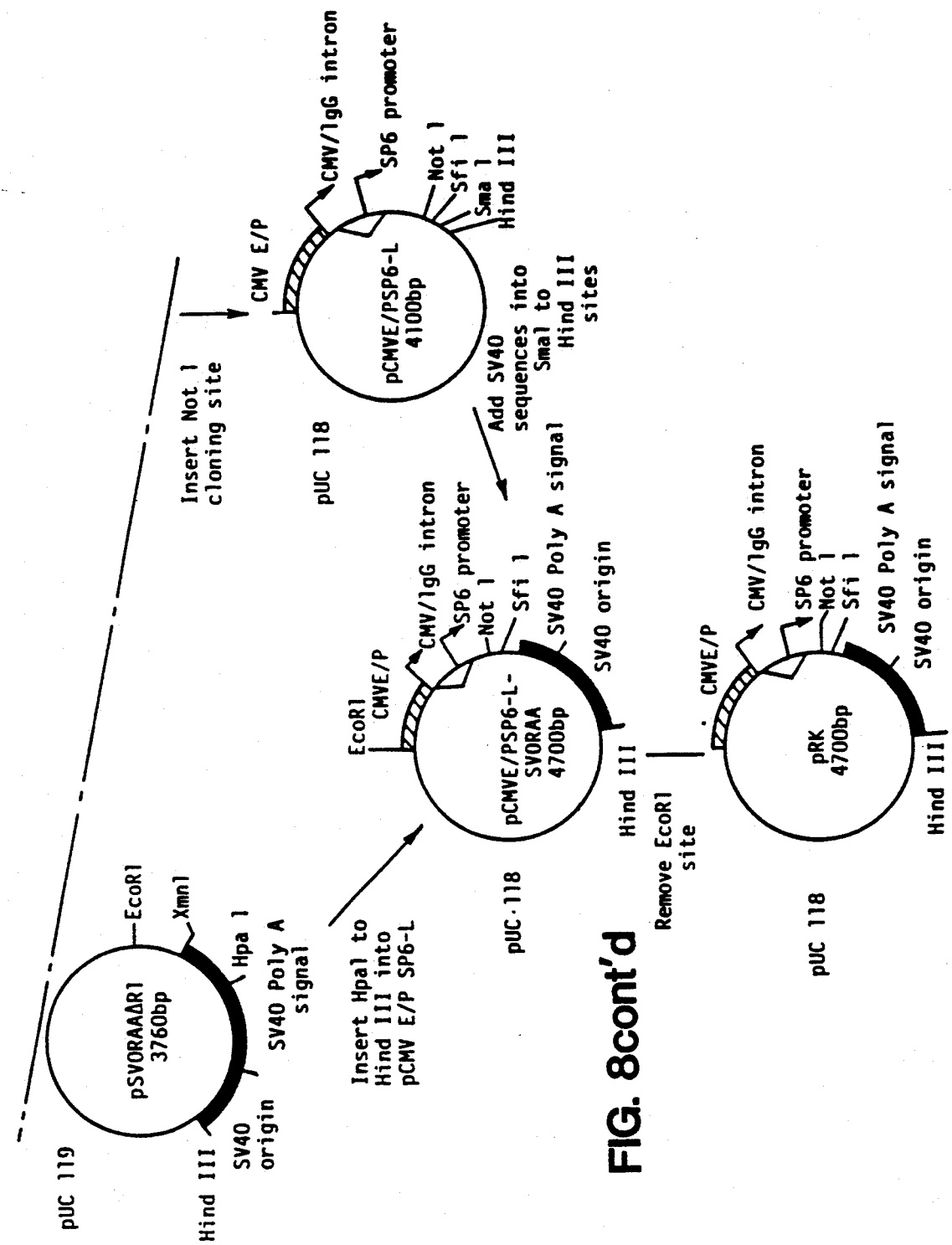

The construction of pRK5 is depicted in FIG. 8. The starting plasmid for construction of pRK5 was pCIS2.8c28D. The base numbers in paragraphs 1 through 6 refer to pCIS2.8c28D with base one of the first T of the EcoRI site preceding the CMV promoter. The cytomegalovirus early promoter and intron and the SV40 origin and polyA signal were placed on separate plasmids.

1. The cytomegalovirus early promoter was cloned as an EcoRI fragment from pCIS2.8c28D (9999-1201) into the EcoRI site of pUC118 described above. Twelve colonies were picked and screened for the orientation in which single-stranded DNA made from pUC118 would allow for the sequencing from the EcoRI site at 1201 to the EcoRI site at 9999. This clone was named pCMVE/P.

2. Single-stranded DNA was made from pCMVE/P in order to insert an SP6 (Green, MR et al., *Cell*, 32: 681-694 [1983]) promoter by site-directed mutagenesis. A synthetic 110 mer that contained the sequences from −69 to +5 of SP6 promoter (see *Nucleic Acids Res.*, 12: 7041 [1984], FIG. 1) were used along with 18-bp fragments on either end of the oligomer corresponding to the CMVE/P sequences. Mutagenesis was done by standard techniques and screened using a labeled 110 mer at high and low stringency. Six potential clones were selected and sequenced. A positive clone was identified and labeled pCMVE/PSP6.

3. The SP6 promoter was checked and shown to be active, for example, by adding SP6 RNA polymerase and checking for RNA of the appropriate size.

4. A Cla-NotI-Sma adapter was synthesized to encompass the location from the ClaI site (912) to the SmaI site of pUC118 in pCMVE/P (step 1) and pCMVE/PSP6 (step 2). This adapter was ligated into the ClaI-SmaI site of pUC118 and screened for the correct clones. The linker was sequenced in both and clones were labeled pCMVE/PSP6-L and pCMVE/P-L.

5. pCHVE/PSP6-L was cut with SmaI (at linker/pUC118 junction) and HindIII (in pUC118). A HpaI (5573)-to-HindIII (6136) fragment from pSVORAA-ΔRI 11, described below, was inserted into SmaI-HindIII of pCMVE/PSP6-L. This ligation was screened and a clone was isolated and named pCMVE/PSP6-L-SVORAAΔRI.

a) The SV40 origin and polyA signal was isolated as the XmnI (5475) - HindIII (6136) fragment from pCIS2.8c28D and cloned into the HindIII to SmaI sites of pUC119 (described in Vieira and Messing, op. cit.). This clone was named pSVORAA.

b) The EcoRI site at 5716 was removed by partial digestion with EcoRI and filling in with Klenow. The colonies obtained from self-ligation after fill-in were screened and the correct clone was isolated and named pSVORAAΔRI 11. The deleted EcoRI site was checked by sequencing and shown to be correct.

c) The HpaI (5573) to HindIII (6136) fragment of pSVORAAΔRI 11 was isolated and inserted into pCMVE/PSP6-L (see 4 above).

6. pCMVE/PSP6-L-SVOrAAΔRI (step 5) was cut with EcoRI at 9999, blunted, and self-ligated. A clone without an EcoRI site was identified and named pRK.

7. pRK was cut with SmaI and BamHI. This was filled in with Klenow and religated. The colonies were screened. A positive clone was identified and named pRKΔBam/Sma3.

8. The HindIII site of pRKDBam/Sma3 was converted to a HpaI site using a converter. (A converter is a piece of DNA used to change one restriction site to another. In this case one end would be complementary to a HindIII sticky end and the other end would have a recognition site for HpaI.) A positive clone was identified and named pRKΔBam/Sma, HIII-HpaI 1.

9. pRKΔBam/Sma, HIII-HpaI 1 was cut with PstI and NotI and an EcoRI-HindIII linker and HindIII-EcoRI linker were ligated in. Clones for each linker were found. However, it was also determined that too many of the HpaI converters had gone in (two or more converters generate a PvuII site). Therefore, these clones had to be cut with HpaI and self-ligated.

10. RI-HIII clone 3 and HIII-RI clone 5 were cut with HpaI, diluted, and self-ligated. Positives were identified. The RI-HIII clone was named pRK5.

C. Construction of pRK5.ibp1.1

FIG. 9 depicts the construction of pRK5.ibp1.1. A 4710-bp EcoRI/SmaI fragment of pRK5 was isolated. Following isolation of the pRK5 fragment, a 934-bp PflMI/PvuII fragment containing nearly all of the BP53 coding region was isolated from pibp.118.1. This fragment was generated by first cleaving pibp.118.1 with BamHI (to remove a nearby fragment) and PvuII followed by digestion with PflMI. The PvuII and PflMI sites immediately 3' of the coding region overlap, and thus cleavage first with PvuII prevents subsequent cleavage with PflMI, leaving one blunt end on the 934-bp isolated fragment. Because PflMI cleavage at the 5' end of the coding region removes the initiating codon ATG, the 5' terminus was reconstructed using an oligonucleotide oibp.11, the sequence of which is given below.

```
EcoRI                                      PflMI
5'-AATTCCACC ATGCAGCGGG CGCGACCCAC GCT-3'
    3'-GGTGG TACGTCGCCC GCGGTGGGTG-5'
```

The three-part ligation of these fragments yielded the expression vector, pRK5.ibp1.1.

D. Expression of Human BP53

Human embryonic kidney cells transformed with adenovirus E1a dn E1b (293s) have been described by Graham et al., *J. Gen. Virol.*, 36: 59-73 (1977). These cells and monkey kidney cells (COS cells) were transfected with the above-described expression vector pRK5.ibp1.1 (or a control plasmid that expresses a secreted form of the human growth hormone receptor described by Leung et al., op. cit.) by the calcium phosphate method of Gorman, in *DNA Cloning*, D. M. Glover, ed. (IRC Press, Oxford, 1985), vol. 2, pp. 143-190. After 24 hours, the cells were changed to a serum-free medium for an additional 48-hour incubation. This serum-free medium was then assayed for BP53 (FIG. 10).

EXAMPLE IV

Assays for BP53

Radioimmunoassay for BP53 (FIG. 10a) was performed as described by Baxter and Martin, *J. Clin. Invest.*, op cit with antisera R-7 (additional bleed from the same rabbit that yielded antiserum R1- 4[Martin and Baxter (1985), op. cit.]) at a 1:10,000 final dilution. Antiserum R1-4 from which antisera R-7 was derived was prepared as follows. A 60K BP was prepared from Cohn Fraction IV of human plasma. Briefly, Cohn paste was extracted with 2M acetic acid, 75 mM NaCl, pH 3.0, and the endogenous IGFs removed by adsorption onto SO-Sephadex (Pharmacia, Sydney, Australia). After a series of stepwise increases in pH, each followed by centrifugation to remove insoluble proteins, the extract, at pH 7.0, was passed through a column of approx. 3 mg human IGF-II covalently bound to agarose gel. The gel was washed to remove contaminating proteins, and the BP was eluted with 0.5M acetic acid, pH 3.0. Final purification was achieved by reverse-phase HPLC on a Hi-Pore RP-318 column (Bio-Rad, Richmond, Calif.) eluted with a 15-60% gradient of acetonitrile in 0.1% trifluoroacetic acid.

Three rabbits (New Zealand White) aged 6 months were injected sc with approximately 750 μg 60 K BP (purified only to the affinity chromatography step) in complete Freund's adjuvant, at several dorsal sites. Two, four and eight weeks later, each animal received approximately 250 μg BP without adjuvant in the thigh muscle, and 8 days after the final boost, the serum of one rabbit (antiserum R1-4) was judged to be of a titer suitable for RIA.

The RIA for BP53 was performed in 10×75-mm polystyrene tubes, in a buffer containing 0.1M sodium phosphate, pH 6.5, 0.02% sodium azide, and 0.25% bovine albumin. Incubation mixtures (500 μl total volume) consisted of appropriately diluted samples or standards (50 μl), antisera R-7 at a final dilution of 1:10,000 (100 μl), BP-IGF-I tracer, 10,000 cpm or 0.5 ng (100 μl), and assay buffer (250 μl), added in that order and vortex mixed.

After 16 h incubation at 22° C., 1 μl normal rabbit serum and 50 μl goat anti-rabbit immunoglobulin (Tg) (Bio-BIA, Montreal, Canada) were added and, after a further 30-min incubation, 1 ml of ice-cold 6% polyethylene glycol solution (PEG 6000; Merck Chemical Div., Merck & Co., Inc., Rahway, N.J.) in 0.15M sodium chloride was added, and tubes were centrifuged 20 min at 4,200 rpm in a Beckman J-6 centrifuge cooled to 2° C. Supernatants were decanted, and the radioactivity in the pellets determined in a gamma counter. Radioactivity added to each assay 7633 cpm; non-specific background, 343 cpm; 100% specific binding, 1711 cpm. The binding and binding competition assays (FIGS. 10b–10d) were performed as described by Martin and Baxter, *J. Biol. Chem.*, op. cit. Thus, samples were incubated 90 min at 22° C. with approximately 20,000 cpm (0.1 ng) of $^{125}$I-IGF-II in 0.3 ml final volume of 50 mM sodium phosphate buffer, pH 6.5, containing 0.25% bovine albumin. To separate bound and free tracer, an ice-cold, rapidly stirred suspension of charcoal, 5 mg in 1 ml of assay buffer containing 0.2 mg of protamine sulfate, was added, and after 8 min at 2° C., the mixture was centrifuged 20 min at 4,200 rpm in a Beckman J-6 centrifuge. Aliquots of 0.65 ml of supernatant, representing half of the reaction mixture, were counted in a γ counter. In competitive binding studies on pure BP, the assay protocol was similar, except that either $^{125}$IGF-I (7,000-8,000 cpm, 20 pg) or $^{125}$IGF-II (6,000-7,000 cpm, 40 pg) was used as tracer. Free and bound ligand were separated by immunoprecipitation with antiserum R-7 at 1:300 final dilution. Radioactivity added was about 14,500 cpm of $^{125}$I-IGF-I (200 Ci/g) or 6300 cpm of $^{125}$-IGF-II (80 Ci/g). Scatchard analysis was performed with the computer program LIGAND as described by Munson and Rodbard, *Anal. Biochem.*, 107: 220-239 (1980). The Scatchard data for the transiently expressed BP53 are provided in FIGS. 10c and 10d.

EXAMPLE V

Binding Protein Assay of IGF

According to the following protocol, BP53 can be used to indicate whether IGF-I or IGF-II capable of binding to BP53 is present in a sample. This assay could be implemented in several ways. For instance, the BP53 could be coupled to a 96-well microtiter plate and aliquots of the samples containing IGF-I or IGF-II could be incubated with the bound BP53 in the presence of a fixed amount of authentic IGF-I or IGF-II with biotin coupled to it. After a 4-6-hour incubation, the solutions would be removed and the plates washed to remove unbound IGF-I or IGF-II. Adding avidin coupled to horseradish peroxidase and incubating would form a complex with the IGF-biotin conjugate. Again, the plates would be washed and HRP substrate added. Color would develop most in wells containing samples with no IGF. As the sample continued to be incubated, the biotin-IGF conjugate would bind at decreasing levels; hence, the color development would be less. This would give a dose-dependent response that could be calibrated using authentic IGF-I or IGF-II (as appropriate) of known concentrations.

This type of assay would have the advantages of a radioreceptor assay, including the specificity for active ligand capable of binding to the receptor, and the sensitivity and simplicity of an ELISA antibody assay, without the disadvantages of either (i.e., radioactive tracer, non-specificity for active protein).

Pharmaceutical Compositions

BP53, and IGF if desired, can be formulated according to known methods to prepare pharmaceutically useful compositions wherein BP53 (and optionally IGF) is combined in admixture with a pharmaceutically acceptable carrier vehicle. Suitable vehicles and their formulations, inclusive of other human proteins, such as serum albumin, are described, for example, in *Remington's Pharmaceutical Sciences* by E. W. Martin, the disclosure of which is incorporated herein by reference. Generally, BP53 may be stored in phosphate-buffered saline or lyophilized in the presence of an excipient, including sugar alcohols, e.g., mannitol or sorbitol; monosaccharides, e.g., glucose, mannose, galactose, or fructose; oligosaccharides such as maltose, lactose or sucrose; and proteins such as human serum albumin.

The foregoing excipients also may contribute to the stability of BP53 to inactivation or precipitation upon aqueous storage, and may be used together with other stabilizers that are conventional per se. Such stabilizers include chelating agents, e.g., EDTA; antioxidants such as ascorbate or dithiothreitol; amino acids; and nonionic surfactants such as polyethylene glycol or block copolymers of polyethylene and polypropylene glycol.

BP53 is administered to humans or animals for use in binding to circulating or membrane-bound IGF present in vivo and possibly prolonging the half-life of IGF in vivo as described above. In addition, BP53 may be administered together with IGF, preferably IGF-I and/or IGF-II, for metabolically affecting the circulatory system in mammals. BP53 can also be used to deliver IGF-I or IGF-II more effectively to tissues.

Therapeutic BP53 compositions will contain a therapeutically effective dose of BP53 in a pharmaceutically acceptable carrier. The dose, carrier, and route and schedule of administration selected will depend, among other factors, upon each other and upon the disorder or condition to be treated, the medical history of the patient, and the activity of the selected BP53 variant. These factors are readily determined and monitored by the treating physician during the course of therapy. A typical dose will range from about 50 to about 200 $\mu$g/kg, preferably 80-150 $\mu$g/kg, for human therapy, depending on the above factors. If BP53 and IGF are to be administered together, they are typically administered in equimolar amounts, so that the molar dose of IGF will be about the same as the molar dose of BP53 administered.

The carrier for parenteral administration of BP53 is a sterile isotonic aqueous solution, for example, saline for injection or 5% dextrose. These preparations are injected or infused by intranasal, subcutaneous, intravenous, intraperitoneal, or other conventional routes of administration.

BP53 also may be provided in a sustained-release carrier formulation. Suitable examples include semipermeable polymer matrices in the form of shaped articles, e.g., suppositories, or microcapsules. Implantable or microcapsular sustained-release matrices include polylactides (U.S. Pat. No. 3,773,919, EP 58,481), copolymers of L-glutamic acid and gamma-ethyl-L-glutamate (U. Sidman et al., *Biopolymers*, 22 (1): 547-556 (1983)), poly(2-hydroxyethylmethacrylate) (R. Langer et al., *J. Biomed. Mater. Res.*, 15: 167-277 (1981) and R. Langer, *Chem. Tech.*, 12: 98-105 (1982)), ethylene vinyl acetate (R. Langer et al., Id.), or poly-D-(-)-3-hydroxybutyric acid (EP 133,988A). Sustained-release BP53 compositions also include liposomally entrapped BP53. Liposomes containing BP53 are prepared by methods known per se: DE 3,218,121A; Epstein et al., *Proc. Nat'l Acad. Sci.* (USA), 82: 3688-3692 (1985); Hwang et al., *Proc. Nat'l. Acad. Sci.* (USA), 77: 4030-4034 (1980); EP 52,322A; EP 36,676A; EP 88,046A; EP 143,949A; EP 142,641A; Japanese patent application 83-118,008; U.S. Pat. Nos. 4,485,045 and 4,544,545; and EP 102,324A.

We claim:

1. An isolated DNA molecule comprising a sequence that hybridizes, under stringent conditions of 50% formamide with 0.75M NaCl and 0.075M sodium citrate, at 42° C., to the portion of the DNA sequence of FIG. 3 coding for mature BP53 or the preprotein for BP53 and which encodes a BP53 protein that binds to IGF-I or IGF-II, excluding BP28, PP12, and HEP-G2.

2. The DNA molecule of claim 1 further comprising a promoter operably linked to said protein-encoding sequence.

3. The DNA molecule of claim 1 further comprising an origin of replication operative in a unicellular organism.

4. The molecule of claim 1 further comprising a signal sequence-encoding region upstream from and operably linked to the protein-encoding sequence.

5. The molecule of claim 4 wherein the signal sequence is recognized by mammalian host cells.

6. The DNA molecule of claim 1 wherein the BP53 protein is human or porcine BP53.

7. An expression vector for producing an insulin-like growth factor binding protein comprising the DNA molecule of claim 1 operably linked to control sequences for expression of the DNA sequence.

8. A host cell transformed with the expression vector of claim 7.

9. The host cell of claim 8 wherein the cell is prokaryotic.

10. The host cell of claim 8 that is eukaryotic.

11. The host cell of claim 10 that is mammalian.

12. The host cell of claim 11 that is a human embryonic kidney cell or COS cell.

13. The host cells of claim 8 that are from a multicellular organism.

14. The host cells of claim 8 that are from a vertebrate.

15. The host cells of claim 8 that are microbial cells.

16. The host cells of claim 8 that are bacterial, yeast, fungal, insect, plant, or mammalian cells.

17. A method of using a DNA molecule encoding an insulin-like growth factor binding protein to produce said protein, which method comprises culturing the cells of claim 8 to express the DNA sequence encoding the protein.

18. The method of claim 17 further comprising the step of recovering the protein from the host cell culture.

19. A method of using a DNA molecule encoding an insulin-like growth factor binding protein to produce said protein, which method comprises culturing the cells of claim 10 to express the DNA sequence encoding the protein.

20. An isolated DNA molecule comprising the portion of the DNA sequence of FIG. 3 encoding mature BP53 or the preprotein of BP53.

* * * * *